US009499621B2

(12) United States Patent
Trauger

(10) Patent No.: US 9,499,621 B2
(45) Date of Patent: Nov. 22, 2016

(54) FELINIZED ANTIBODIES AND METHODS OF TREATING RETROVIRAL INFECTIONS IN FELINES

(71) Applicant: Richard Trauger, Leucadia, CA (US)

(72) Inventor: Richard Trauger, Leucadia, CA (US)

(73) Assignee: CYTODYN, INC., Vancouver, WA (US)

( * ) Notice: Subject to any disclaimer, the term of this patent is extended or adjusted under 35 U.S.C. 154(b) by 0 days.

(21) Appl. No.: 14/247,680

(22) Filed: Apr. 8, 2014

(65) Prior Publication Data

US 2014/0348829 A1 Nov. 27, 2014

Related U.S. Application Data

(60) Provisional application No. 61/809,773, filed on Apr. 8, 2013.

(51) Int. Cl.

| C07K 16/00 | (2006.01) |
|---|---|
| C07K 16/46 | (2006.01) |
| C07K 16/28 | (2006.01) |
| A61K 39/395 | (2006.01) |
| A61K 45/06 | (2006.01) |

(52) U.S. Cl.
CPC ....... *C07K 16/2845* (2013.01); *A61K 39/3955* (2013.01); *A61K 45/06* (2013.01); *C07K 2317/20* (2013.01); *C07K 2317/24* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| 4,522,811 A | 6/1985 | Eppstein et al. |
| 4,866,186 A | 9/1989 | Thompson et al. |
| 4,965,200 A | 10/1990 | Chen et al. |
| 5,134,124 A | 7/1992 | Nisato et al. |
| 5,159,104 A | 10/1992 | Dabora et al. |
| 5,223,409 A | 6/1993 | Ladner et al. |
| 5,324,510 A | 6/1994 | Wegner et al. |
| 5,393,893 A | 2/1995 | Kubela et al. |
| 5,462,716 A | 10/1995 | Holm |
| 5,695,760 A | 12/1997 | Faanes et al. |
| 5,760,185 A * | 6/1998 | Kimachi ............ C07K 16/085 424/133.1 |
| 5,914,112 A | 6/1999 | Bednar et al. |
| 6,100,407 A | 8/2000 | Van Dalen et al. |
| 6,252,091 B1 | 6/2001 | Zupancic et al. |
| 6,384,238 B1 | 5/2002 | Zilcar |
| 6,472,542 B1 | 10/2002 | Galeazzi et al. |
| 6,541,511 B1 | 4/2003 | Thaper et al. |
| 6,689,869 B2 | 2/2004 | Waldamann et al. |
| 6,872,735 B2 | 3/2005 | Burdick et al. |
| 6,919,077 B2 * | 7/2005 | Kapustay ........... C07K 16/2845 424/130.1 |
| 7,166,638 B2 | 1/2007 | Benedini et al. |
| 7,297,808 B2 | 11/2007 | Benedini et al. |
| 7,304,091 B2 | 12/2007 | Frisvad et al. |
| 7,420,078 B2 | 9/2008 | Ohrlein et al. |
| 7,563,909 B2 | 7/2009 | Benedini et al. |
| 7,855,302 B2 | 12/2010 | Ohrlein et al. |
| 2002/0035274 A1 | 3/2002 | Dalen et al. |
| 2002/0039577 A1 | 4/2002 | Townsend et al. |
| 2003/0176501 A1 | 9/2003 | Tillyer et al. |
| 2004/0101527 A1 | 5/2004 | Horvath |
| 2004/0186313 A1 | 9/2004 | Ohrlein et al. |
| 2004/0235935 A1 | 11/2004 | Vanderbist et al. |
| 2005/0148654 A1 | 7/2005 | Bisgaier et al. |
| 2005/0165084 A1 | 7/2005 | Benedini et al. |
| 2005/0228042 A1 | 10/2005 | Frisvad et al. |
| 2007/0072942 A1 | 3/2007 | Benedini et al. |
| 2008/0090857 A1 | 4/2008 | Benedini et al. |
| 2008/0096908 A1 | 4/2008 | Benedini et al. |
| 2008/0289056 A1 | 11/2008 | Greenberg et al. |
| 2009/0118317 A1 | 5/2009 | Bisgaier et al. |
| 2009/0205061 A1 * | 8/2009 | Li ...................... C07K 14/705 800/14 |
| 2009/0285752 A1 | 11/2009 | Goldenberg et al. |

(Continued)

FOREIGN PATENT DOCUMENTS

| WO | WO 9002809 | 3/1990 |
| WO | WO 9117271 | 11/1991 |

(Continued)

OTHER PUBLICATIONS

MacMillan, M., The 12th Annual Meeting of the Rocky Mountain Virology Association: Current Advances in Virology in the Rocky Mountain Region. iMedPub Journals, Translational Biomedicine, vol. 3 No. 4:1 , Sep. 28-30, 2012.*
Pourhassan, N. A Novel HIV Therapy in Late Stage Clinical Development PRO 140: Humanized Monoclonal Antibody Blocking HIV Infection of T Cells. CytoDyn. retrived Dec. 30, 2015.*
Tanabe-Tochikura, et al., "Anti-Human Immunodeficiency Virus (HIV) Agents are also Potent and Selective Inhibitors of Feline Immunodeficiency Virus (FIV)-Induced Cytopathic Effect: Development of a New Method for Screening of anti-FIV Substances in vitro", Antiviral Res. 19:161-172 (1992).*
Miller et al. Human Immunodeficiency Virus and AIDS: Insights from Animal Lentiviruses. Journal of Virology, Aug. 2000, p. 7187-719.*

(Continued)

*Primary Examiner* — Maher Haddad
(74) *Attorney, Agent, or Firm* — Miller Nash Graham & Dunn LLP; Chandra E. Eidt

(57) ABSTRACT

Provided are felinized antibodies and methods for treating or reducing the likelihood of developing a retroviral infection in a feline, decreasing retroviral virion entry into a feline cell, decreasing retroviral virion budding from a feline cell, or decreasing syncytium transmission in a feline. These methods require the administration of at least one felinized antibody or fragment thereof that specifically binds to CD11a and/or CD18, or ICAM-1, and/or decreases or prevents the binding of LFA-1 (CD11a/CD18 heterodimer) to ICAM-1. Also provided are veterinary compositions and methods of identifying candidate agents useful for treating or reducing retroviral infection in a feline, decreasing retroviral virion entry into a feline cell, decreasing retroviral virion budding from a feline cell, or decreasing syncytium transmission in a feline.

10 Claims, 12 Drawing Sheets

(56) References Cited

U.S. PATENT DOCUMENTS

| | | | |
|---|---|---|---|
| 2010/0092470 | A1 | 4/2010 | Bhatt et al. |
| 2011/0052601 | A1 | 3/2011 | Mohapatra et al. |
| 2011/0054193 | A1 | 3/2011 | Van Den Berg et al. |
| 2013/0022616 | A1* | 1/2013 | Bammert .............. C07K 16/244 424/158.1 |
| 2014/0140997 | A1 | 5/2014 | Trauger |

FOREIGN PATENT DOCUMENTS

| | | | |
|---|---|---|---|
| WO | WO 9201047 | | 1/1992 |
| WO | WO 9202079 | | 2/1992 |
| WO | WO 9209690 | | 6/1992 |
| WO | WO 9215679 | | 9/1992 |
| WO | WO 9218619 | | 10/1992 |
| WO | WO 9301288 | | 1/1993 |
| WO | WO 9640247 | * | 12/1996 |
| WO | WO0103681 | | 1/2001 |
| WO | WO02059114 | | 8/2002 |
| WO | WO2012024650 | * | 2/2012 |
| WO | WO 2012/153122 | | 11/2012 |
| WO | WO 2012/174392 | | 12/2012 |

OTHER PUBLICATIONS

Vajdos et al. Comprehensive functional maps of the antigen-binding site of an anti-ErbB2 antibody obtained with shotgun scanning mutagenesis. J. Mol. Biol. Jul. 5, 2002, 320(2):415-28.*
Brown et al. Tolerance of single, but not multiple, amino acid replacements in antibody VH CDR 2: a means of minimizing B cell wastage from somatic hypermutation? J. Immuno. May 1996, 3285-91.*
Zacks: Promising Antibody Technology for the Treatment of HIV/FIV, pp. 1-4. Feb. 15, 2015.*
Zacks Small-Cap Research. CYDY: Potential acquisition of CCR5 antibody may boost pipeline—Neutral. Apr. 19, 2012 Xiao Cheng. pp. 1-15.*
CYTODYN Annual Report. Form 10-K for the Year Ended May 31, 2015. pp. 1-93.*
Gebhard et al., "Progressive Expansion of an L-Selectin-Negative CD8 Cell with Anti-Feline Immunodeficiency Virus (FIV) Suppressor Function in the Circulation of FIV-Infected Cats," College of Veterinary Medicine, North Carolina State University, pp. 1503-1513, 1999.
Alomg, Chest 124: 740-743, 2003.
Champe et al., J. Biol. Chem. 270: 1388-1394, 1995.
Chintalacharuvu et al., Clin. Immunol. 101: 21-31, 2001.
Cole et al., Monoclonal Antiobodies and Cancer Therapy, Alan R. Liss, Inc., pp. 77-96, 1985.
Frigerio et al., Plant Physiol. 123: 1483-1494, 2000.
Fuchs et al., Bio/Technology 9: 1370-1372, 1991.
Ghetie et al., Proc. Natl. Acad. Sci. U.S.A. 94: 7509-7514, 1997.
Goel et al., Cancer Res. 60: 6964-6971, 2000.
Griffiths et al., EMBO J. 12: 725-734, 1993.
Hay et al., Hum. Antibod. Hybridomas 3: 81-85, 1992.
Huse et al., Science 246: 1275-1281, 1989.
Jarrett et al., Nature 202: 566, 1964.
Johansen et al., J. Immunol. 167: 5185-5192, 2001.
Kohler et al., Nature 256: 495-497, 1975.
Kozbor et al., Immunol. Today 4: 72, 1983.
Nishimura et al., Immunogenetics 50: 369-370, 1999.
Richards, Biologicals 33: 219, 2005.
Saalmuller et al., Cell. Immunol. 236: 51-58, 2005.
Shimojima et al., Microbes Infection 5: 1171-1176, 2003.
Shimojima et al., J. Vet. Med. Sci. 59: 467-169, 1997.
Shimojima et al., Vet. Immunol. Immunopathol. 61: 17-23, 1998.
Wang et al., Biol. Blood Marrow Transplant. 15: 1513-1522, 2009.
Weitz-Schmidt et al., J. Biol. Chem. 279: 46764-46771, 2004.
Welzenbach et al., J. Biol. Chem. 277: 10590-10598, 2002.
Zhao et al., J. Immunol. 25: 396-404, 2002.
Hein et al., "In Vitro Activation of Feline Immunodeficiency Virus in Ramified Microglial Cells from Asymptomatically Infected Cats." Journal of Virology, vol. 75, No. 7: 8090-8095, 2001.
Dobson et al., "Diagnosis and management of leukaemia in dogs and cats," In Practice; 22-31, 2006.
Li et al., "Efalizumab binding to the LFA-1 αL I domain blocks ICAM-1 binding via steric hindrance," PNAS; 4349-4354, 2009.
Petruzzelli et al., "Activation of Lyphocyte Function-Associated Molecule-1 (CD11a/CD18) and Mac-1 (CD11b/CD18) Mimicked by an Antibody Directed Against CD18l," The Journal of Immunology; 854-866, 1995.
Rice et al., Inducible Cell Adhesion Molecule 110 (INCAM-110) Is an Endothelial Receptor for Lymphocytes A CD11/CD18-independent Adhesion Mechanism,: J. Exp. Med.; 1369-1374, 1990.
Rizzuto et al., "Contribution of Virion ICAM-1 to Human Immunodeficiency Virus Infectivity and Sensitivity to Neutralization," Journal of Virology; 4847-4851, 1997.
Shimojima et al., "Phenotypic changes in CD8+ peripheral blood lymphocytes in cats infected with feline immunodeficiency virus," Microbes and Infection; 1171-1176, 2003.

* cited by examiner

| Antibody # | Heavy chain | Light chain |
|---|---|---|
| #1 (Parental) | 7262 (Parental HC) | 7263 (Parental LC) |
| #15 | 7301 (Felinized HC 3) | 7303 (Felinized LC 2) |

Figure 6
SEQ. ID NO: 1

>7299 (Felinized HC 1)
QVQLVQSGAEVRKPGASVKIPCKASGYTFTSYYIHWLRQTPEQGLEWMGWIYVGDGNTRYNQKFQGRLTLTADKSTS
TAYMELSSLRSADTAIYFCARGGNGYFDYWGQDTLVTVSS CAGGTGCAGCTGGTGCAGTCTGGCGCTGAAGTGCGAAAGCCTGGCGCCTCCGTGAAGATTTTCTGCAAGGCCTCCGG
CTACACCTTCACCAGCTACTACATCGACTGGCTGCGGCAGACCCCTGAGCAGGGCCTGGAATGGATGGGCTGGATCT
ATGTGGGCGACGGCAACACCCGGTACAACCAGAAGTTCCAGGGCCGGCTGACCCTGACCGCCGACAAGTCTACCTCC
ACCGCCTACATGGAACTGTCCTCCCTGAGATCCGCCGACACCGCCATCTACTTTTGCGCCAGAGGCGGCAACGGCTA
CTTCGACTACTGGGGCCAGGACACCCTCGTGACCGTGTCCTCT

Figure 7
SEQ. ID NO: 2

>7300 (Felinized HC 2)
QVQLVQSGAEVRKPGASVKIPCKASGYTFTSYYIHWLRQTPEQGREWIGWIYVGDGNTRYNEKFQGRLTLTADKSTS
TAYMELSSLRSADTAIYFCARGGNGYFDYWGQPTLVTVSS CAGGTGCAGCTGGTGCAGTCTGGCGCTGAAGTGCGAAAGCCTGGCGCCTCCGTGAAGATTTCTGCAAGGCCTCCGG
CTCACCTTCACCAGCTACTACATCCACTGGCTGCGGCAGACCCCCGAGCAGGGAAGAGAATGGATCGGCTGGATCT
ACGTGGGCGACGGCAACACCCGGTACAACGAGAAGTTCCAGGGCCGGCTGACCCTGACCGCCGACAAGTCTACCTCC
ACCGCCTACATGGAACTGTCCTCCCTGAGATCCGCCGACACCGCCATCTACTTTTGCGCCAGAGGCGGCAACGGCTA
CTTCGACTACTGGGGCCAGGACACCCTCGTGACCGTGTCCTCT

Figure 8
SEQ. ID NO: 3

>7301 (Felinized HC 3)
QVQLVQSGAEVRIPGASVEIPCKASGYTFTSYYIHWVRQSPAQGREWMGWIYVGDGNTKYNERFQGRLTLEADKSTS
TAYMELSSLRSADTAMYFCARGGNGYFDYWGQGALVTVSS CAGGTGCAGCTGGTGCAGTCTGGCGCTGAAGTGCGAACCCTGGCGCCTCCGTGAAGATTTCTGCAAGGCCTCCGG
CTACACCTTCACCAGCTACTACATCCACTGGGTGCGACAGAGCCCTGCCCAGGGCAGAGAATGGATGGGCTGGATCT
ATGTGGCGACGGCAACACCAAGTACAACGAGCGGTTCCAGGGCCGGCTGACCCTGACCGCTGACAAGTCTACCTCC
ACCGCCTACATGGAACTGTCCTCCCTGAGATCCGCCGACACCGCCATGTACTTTGCGCCAGAGGCGGCAACGGCTA
CTTCGACTATTGGGGCCAGGGCGCTCTCGTGACCGTGTCCTCT

Figure 9
SEQ. ID NO: 4

>7302 (Felinized LC 1)
DIVMTQTPLSLSVTPGEPASISCRASQDVSTALNWYLQKPGQSPRLLIYWASNRHSGVPDRFSGSGSGTDYTLRISR
VEADDVGVYYCQQHYSSSLITFGPGTKLEI GACATCGTGATGACCCAGACCCCTCTGTCCCTGTCTGTGACACCTGGCGAGCCTGCCTCCATCTCCTGCAGAGCCTC
CCAGGATGTGTCTACCGCCCTGAACTGGTATCTGCAGAAGCCTGGCCAGTCTCCTCGGCTGCTGATCTACTGGGCCT
CCAACAGACACTCTGGCGTGCCCGACAGATTCTCCGGCTCTGGCTCTGGCACCGACTACACCCTGCGGATCTCCAGA
GTGGAAGCCGACGACGTGGGCGTGTACTACTGCCAGCAGCACTACTCCTCCAGCCTGACCTTTGGCCCTGGCACCAA
GCTGGAAATC

Figure 10
SEQ. ID NO: 5

>7303 (Felinized LC 2)
DIVMTQTPLSLSVTPGEPASISCRASQDVSTALAWYLQKPGQSPRLLIYWASTRESGVPDRFSGSGSGTDYTLRISR
VEADDVGVYYCQQHYSSLTFSPGTKLEI GACATCGTGATGACCCAGACCCCTCTGTCCCTGTCTGTGACACCTGGCGAGCCTGCCTCCATCTCCTGCAGAGCCTC
CCAGGATGTGTCTACCGCCCTGGCCTGGTATCTGCAGAAGCCTGGCCAGTCTCCTCGGCTGCTGATCTACTGGGCCT
CCACTAGAGACTTCTGGCGTGCCCGACAGATTCTCCGGCTCTGGCTCTGGCACCGACTACACCCTGCGGATCTCCAGA
GTGGAAGCCGACGACGTGGGCGTGTACTACTGCCAGCAGCACTACTCCTCCAGCCTGACCTTTGGCCCTGGCACCAA
GCTGGAAATC

Figure 11
SEQ. ID NO: 6

>7304 (Felinized LC 3)
DIVMTQPPSVSGALGQTVTISCAGSQDVSTRVAWYQQLTGKAPTLLIYWASTRESSVPDRFSGSGSGTTYSLTITGL
QAEDEADYYCQQHYSSSLTFGADTVLQA GACATCGTGATGACCCAGCCCCCTTCTGTGTCTGGCGCTCTGGGCCAGACCGTGACCATCTCTTGTGCCGGCTCTCA
GGACGTGTCCACCCGCGTGTGGCTTGGTATCAGCAGCTGACCGGCAAGGCCCCCACCCTGCTGATCTACTGGGCCTCCA
CCAGACACTCCTCCGTGCCTGACAGATTCTCCGGCTCTGGCTCCGGCACCACCTACTCCCTGACAATCACCGGACTG
CAGGCCGAGGACGAGGCCGACTACTACTGCCAGCAGCACTACTCCTCCAGCCTGACCTTTGGCGCCGACACCGTGCT
GCAGGCT

Figure 12
SEQ. ID NO: 7

>Feline IgG1 heavy chain constant region
ASTTAPSVFPLAPSCGTTSGATVALACLVLGYFPEPVTVSWNSGALTSGVRTFPAVLQASGLYSLSSMVTVPSSRWL
SDTFTCNVAHPPSNTKVDKTVRKTDHPFGPKPCDCPKCPPPEMLGGPSIFIFPPKPKDTLSISRTPEVTCLVVDLGP
DDSDVQITWFVDNTQVYTAKTSPREEQFNSTYRVVSVLPILEQDWLKGKEFKCKVNSKSLPSPIEKTISKAKGQPHE
PQVYVLPPAQEELSRNKVSVTCLIKSFHPPDIAVEWEITGQPEPENNYRTTPPQLDSDGTYFVYSKLSVDRSHWQRG
NTYTCSVSHEALHSHHTQKSLTQSPG GCTAGCACCACCGCCCCTTCCGTGTTCCCTCTGGCCCCTTCTTGTGGCACCACCTCTGGCGCTACAGTGGCCCTGGC
TTGTCTGGTGCTGGGCTACTTCCCTGAGCCCGTGACCGTGTCCTGGAACTCTGGCGCTCTGACATCGGCGTGCACA
CCTTCCCTGCTGTGCTGCAGGCTTCCGGCCTGTACTCCCTGTCCTCTATGGTCACCGTGCCTCCAGCCGGTGGCTG
TCCGATACCTTCACCTGTAACGTGGCCCACCCTCCCAGCAACACCAAGGTGGACAAGACCGTGCGGAAGACCGACCA
CCCTCCTGGCCCTAAGCCTTGCGACTGCCTAAGTGCCCACCCCCTGAAATGCTGGGCGGACCTAGCATCTTCATCT
TCCCACCCAAGCCCAAGGACACCCTGTCCATCTCCCGGACCCCTGAAGTGACCTGCCTGGTCGTGGATCTGGGCCCT
GACGACTCCGACGTGCAGATCACTTGGTTTGTGGACAACACCCAGGTGTACACAGCCAAGACCTCCCCCGGAGAGGA
ACAGTTCAACTCCACCTACCGGGTGGTGTCCGTGCTGCCCATCCTGGAGCAGGACTGGCTGAAGGGCAAGGAATTCA
AGTGCAAAGTGAACCTCAAGTCCCTGCCCTCCCCCATCGAGAAGACCATCTCTAAGGCCAAGGGCCAGCCTCACGAG
CCTCAGGTGTACGTGCTGCCTCCCGCCCAGGAAGAACTGTCCCGGAACAAAGTGTCCGTGACCTGTCTGATCAAGTC
CTTCCACCCACCCGATATCGCCGTGGAATGGGAGATCACCGGCCAGCCCGAGCCCGAGAACAACTACAGAACCACCC
CTCCCCAGCTGGACTCTGACGGCACCTACTTCGTGTACTCCAAGCTGTCCGTGGACAGATCCCACTGGCAGCGGGGC
AACACCTACACCTGTTCCGTGTCTCACGAGGCCCTGCACTCCCACCACACCCAGAAGTCTCTGACCCAGTCCCCCGG
CTAGTAA

Figure 13
SEQ. ID NO: 8

>Feline kappa light chain constant region
RSDAQPSVFLFQPSLDELHTGSASIVCILNDFYPREVNVKWKVDGVVQTKASKESTTEQNSKDSTYSLSSTLTNSR
TEYQSHEKFSCEVTHKSLASTLVKSFNRSECQRE AAGAGATCCGACGCCCAGCCCTCCGTGTTCCTGTTCCAGCCTTCTCTGGACGAGCTGCACACCGGCTCCGCCTCCAT
CGTGTGCATCCTGAACGACTTCTACCCCAAAGAAGTGAACGTGAAGTGGAAGGTGGACGGCGTGGTCCAGACCAAGG
CCTCCAAAGAGTCCACCACCGAGCAGAACTCCAAGGACTCCACCTACTCCCTGTCCTCCACCCTGACCAATGTCCGG
ACCGAGTACCAGTCCCACGAGAAGTTCAGCTGCGAAGTGACCCACAAGTCCCTGGCCAGCACCCTGGTGAAGTCCTT
CAACAGATCCGAGTGCCAGAGAGAGTAA

FELINIZED ANTIBODIES AND METHODS OF TREATING RETROVIRAL INFECTIONS IN FELINES

RELATED APPLICATIONS

This application claims priority to U.S. provisional patent application Ser. No. 61/809,773 filed on Apr. 8, 2013, the contents of which are fully incorporated herein by reference.

TECHNICAL FIELD

This invention relates generally to felinized antibodies and methods of treating retroviral infections in felines.

BACKGROUND

Felines are susceptible to infection by retroviruses (e.g., feline immunodeficiency virus (FIV) and feline leukemia virus (FELV)). FIV is the causative agent of feline immunodeficiency disease syndrome. FELV is caused by a feline retrovirus that is similar to human leukemia virus in humans. Feline leukemia virus induces the uncontrolled growth of blood cells.

Feline retroviruses affect a significant portion of the feline population. For example, approximately 2.5% to 4.4% of cats worldwide were estimated to be infected with FIV in 2005 (Richards, *Biologicals* 33:219, 2005). Approximately 0.5% of domestic felines are persistently infected with FELV. Successful treatment of FIV and FELV infection in felines (e.g., domestic and feral felines) is desired.

SUMMARY

The present invention is based, at least in part, on the discovery that an antibody that specifically binds to the cellular antigen LFA-1 (CD11a/CD18 heterodimer) reduces retroviral infection of feline cells in vitro. Provided herein are methods of treating retroviral infections in felines by administering one or more agents that specifically bind to CD11a, CD18, an epitope formed by both CD11a and CD18, or ICAM-1 present on the surface of a feline cell (e.g., a non-infected feline cell) or present on the surface of a retroviral virion or syncytium. In some embodiments, the one or more agents decrease the binding of LFA-1 to ICAM-1. Also provided are methods of reducing or preventing retroviral virion entry into a feline cell (e.g., a non-infected feline cell) or reducing or preventing retroviral virion budding from a feline cell by administering at least one agent that specifically binds to CD11a, CD18, an epitope formed by both CD11a and CD18, or ICAM-1, and/or decreases the binding of LFA-1 to ICAM-1. Also provided are methods of reducing or preventing syncytium transmission in a feline by administering at least one agent that specifically binds to CD11a, CD18, an epitope formed by both CD11a and CD18, or ICAM-1, and/or prevents or decreases LFA-1 binding to ICAM-1.

In some embodiments of all of the methods described herein, the at least one agent decreases the interaction (e.g., decreases the $K_{on}$ rate, increases the $K_{off}$ rate, increases the $K_D$, and/or decreases the $K_A$) of LFA-1 with ICAM-1. The LFA-1 can be present on the surface of a feline cell (e.g., a non-infected feline cell) with ICAM-1 present on the surface of a retroviral virion or syncytium. In some embodiments, the LFA-1 can be present on the surface of a retroviral virion or syncytium with ICAM-1 present on the surface of a feline cell (e.g., a non-infected feline cell). In some embodiments, the at least one agent decreases the ability of LFA-1 or ICAM-1 to contribute to virion entry into a feline cell (e.g., a non-infected feline cell) or decreases the ability of LFA-1 or ICAM-1 to contribute to virion budding. In some embodiments, the at least one agent decreases the ability of LFA-1 or ICAM-1 to contribute to syncytium transmission in a feline. In any of the embodiments described herein, LFA-1 may be present on the surface of a feline cell (e.g., a non-infected feline cell) or on the surface of a retroviral virion or syncytium. In any of the embodiments described herein, ICAM-1 may be present on the surface of a feline cell (e.g., a non-infected feline cell) or on the surface of a retroviral virion or syncytium.

Compositions containing at least one agent that specifically binds to CD11a, CD18, an epitope formed by both CD11a and CD18, or ICAM-1, and/or decreases the interaction of LFA-1 with ICAM-1 are also provided, as well as methods of identifying such agents.

Provided are methods for treating a retrovirus infection in a feline. These methods include administering to a feline at least one (e.g., one, two, three, or four) small molecule that decreases LFA-1 binding to ICAM-1, where the at least one small molecule is administered in an amount sufficient to treat a retrovirus infection. Also provided are methods for treating a retrovirus infection in a feline that include administering to a feline at least one (e.g., one, two, three, or four) antibody or antigen-binding fragment thereof that specifically binds to CD11a and/or CD18 (binds specifically to CD11a, CD18, or an epitope that is formed by both CD11a and CD18), wherein the at least one antibody or antigen-binding fragment thereof is administered in an amount sufficient to treat a retrovirus infection. Also provided are methods for treating a retrovirus infection in a feline that include administering to a feline at least one (e.g., one, two, three, or four) antibody or antigen-binding fragment thereof that specifically binds to ICAM-1, wherein that at least one antibody or antigen-binding fragment thereof is administered in an amount sufficient to treat a retrovirus infection.

Also provided are methods for reducing retroviral virion entry into a feline cell (e.g., a non-infected feline cell) or retroviral virion budding from a feline cell in a feline. These methods include administering to a feline at least one (e.g., one, two, three, or four) small molecule that decreases LFA-1 binding to ICAM-1, wherein the at least one (e.g., one, two, three, or four) small molecule is administered in an amount sufficient to reduce retroviral virion entry into a feline cell or retroviral virion budding from a feline cell. Also provided are methods for reducing retroviral virion entry into a feline cell or retroviral virion budding from a feline cell in a feline that include administering at least one (e.g., one, two, three, or four) antibody or antigen-binding fragment thereof that specifically binds to CD11a and/or CD18 (binds specifically to CD11a, CD18, or an epitope formed by both CD11a and CD18), wherein the at least one antibody or antigen-binding fragment thereof is administered in an amount sufficient to reduce retroviral virion entry into a feline cell or retroviral virion budding from a feline cell. Also provided are methods for reducing retroviral virion entry into a feline cell or retroviral virion budding from a feline cell in a feline that include administering at least one (e.g., one, two, three, or four) antibody or antigen-binding fragment thereof that specifically binds to ICAM-1, wherein the at least one antibody or antigen-binding fragment thereof is administered in an amount sufficient to reduce retroviral virion entry into a feline cell or retroviral virion budding from a feline cell.

Also provided are methods of reducing syncytium transmission in a feline. These methods include administering to a feline at least one (e.g., one, two, three, or four) small molecule that decreases LFA-1 binding to ICAM-1, wherein the at least one small molecule is administered in an amount sufficient to reduce syncytium transmission in a feline. Also provided are methods of reducing syncytium transmission in a feline that include administering to a feline at least one (e.g., one, two, three, or four) antibody or antigen-binding fragment thereof that specifically binds to CD11a and/or CD18 (binds specifically to CD11a, CD18, or an epitope formed by both CD11a and CD18), wherein the at least one antibody or antigen-binding fragment thereof is administered in an amount sufficient to reduce syncytium transmission in a feline. Also provided are methods of reducing syncytium transmission in a feline that include administering to a feline at least one (e.g., one, two, three, or four) antibody or antigen-binding fragment thereof that specifically binds to ICAM-1, where the at least one antibody or antigen-binding fragment thereof is administered in an amount sufficient to reduce syncytium transmission in a feline.

In some embodiments, the at least one antibody or antigen-binding fragment thereof binds specifically to CD11a and/or CD18 (binds specifically to CD11a, CD18, or an epitope formed by both CD11a and CD18), or ICAM-1. In some embodiments, the at least one antibody or antigen-binding fragment thereof decreases LFA-1 binding to ICAM-1. In any of the methods described herein, the at least one antibody is a monoclonal antibody.

In some embodiments, the at least one antibody or antigen-binding fragment thereof that specifically binds to CD11a is an antibody or an antigen-binding fragment thereof that contains at least one complementary determining region (CDR) from the light chain or the heavy chain of TS1/22 antibody (produced from ATCC deposit number HB202). In some embodiments, the at least one antibody or antigen-binding fragment thereof is an antibody or an antigen-binding fragment thereof that contains the three CDRs from the light chain of TS1/22 antibody or the three CDRs from the heavy chain of TS1/22 antibody. In some embodiments, the at least one antibody or antigen-binding fragment thereof is an antibody or an antigen-binding fragment thereof that contains the three CDRs from the light chain of TS1/22 antibody and the three CDRs from the heavy chain of TS1/22 antibody. In some embodiments, the at least one antibody or antigen-binding fragment thereof is TS1/22 antibody or an antigen-binding fragment of TS1/22 antibody.

In some embodiments, the at least one antibody is a feline antibody or an antigen-binding fragment thereof, or a felinized antibody or an antigen-binding fragment thereof. In some embodiments of all of the methods described herein, the antibody is a single-chain antibody (e.g., a single-domain antibody). In some embodiments, the at least one antigen-binding fragment thereof is selected from the group consisting of: a Fab fragment, a $F(ab')_2$ fragment, and a scFv fragment. In some embodiments, the at least one small molecule is lovastatin, simvastatin, a lovastatin derivative (e.g., a 6-exomethylene-modified, an 8-acyl-modified, or an alkylated lovastatin), a simvastatin derivative, LFA703, LFA451, LFA878, or XVA143, or a salt, solvate, or hydrate thereof.

In some embodiments, the at least one small molecule is:

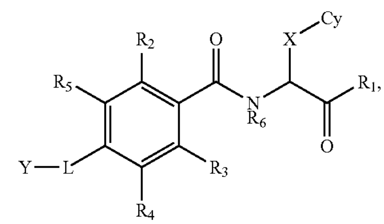

where

Cy is a non-aromatic carbocycle or heterocycle, optionally substituted with hydroxyl, mercapto, thioalkyl, halogen, oxo, thio, amino, aminoalkyl, amidine, guanidine, nitro, alkyl, alkoxy, or acyl; X is a divalent hydrocarbon chain, optionally substituted with hydroxyl, mercapto, halogen, amino, aminoalkyl, nitro, oxo, or thio, and optionally interrupted with N, O, S, SO, or $SO_2$; Y is a carbocycle or heterocycle, optionally substituted with hydroxyl, mercapto, halogen, oxo, thio, thioalkyl, amino, aminoalkyl, carbocycle, or heterocycle ring, hydrocarbon, a halo-substituted hydrocarbon, amino, amidine, guanidine, cyano, nitro, alkoxy, or acyl; L is a divalent hydrocarbon chain, optionally substituted with hydroxyl, halogen, oxo, or thio; $R_1$ is H, OH, amino, O-carbocycle, or alkoxy, optionally substituted with amino, a carbocycle, or heterocycle; $R_{2-5}$ are independently H, hydroxyl, mercapto, halogen, cyano, amino, amidine, guanidine, nitro, or alkoxy; or $R_3$ or $R_4$ together form a fused carbocycle or heterocycle, optionally substituted with hydroxyl, halogen, oxo, thio, amino, amidine, guanidine, or alkoxy; and $R_6$ is H or a hydrocarbon chain, optionally substituted with a carbocycle or a heterocycle. In some embodiments, at least one small molecule can be any of the molecules shown in FIGS. 1A-F. Any of the small molecules described herein can be in the form of a salt, solvate, or hydrate.

In some embodiments, the at least one small molecule and/or the at least one antibody or antigen-binding fragment thereof is administered intravenously, intraarterially, ocularly, orally, subcutaneously, intraperitoneally, or intramuscularly. In some embodiments, the at least one small molecule is administered orally. In some embodiments, the at least one antibody or antigen-binding fragment thereof is administered intravenously.

In some embodiments where the feline is administered at least one antibody or antigen-binding fragment thereof (e.g., any of the antibodies or antigen-binding fragments described herein), the feline is further administered at least one (e.g., one, two, three, or four) small molecule (e.g., any of the small molecules described herein) that prevents LFA-1 from binding to ICAM-1. In some embodiments, the at least one small molecule and the at least one antibody or antigen-binding fragment thereof are administered in the same composition. In some embodiments, the at least one small molecule and the at least one antibody or antigen-binding fragment thereof are administered by different routes of administration.

In some embodiments of any of the methods described herein, the administering results in a decrease (e.g., a significant or observable decrease) in the severity, frequency, or duration of at least one symptom of retroviral infection in the feline. In some embodiments of any of the methods described herein, the administering results in a decrease (e.g., a statistically significant decrease) in retroviral titer in the feline. In some embodiments of any of the methods described herein, the administering results in an increase (e.g., a statistically significant increase) in the ratio of CD4$^+$ T-cells to CD8$^+$ T-cells in the feline. In some embodiments of any of the methods described herein, the at least one small molecule and/or the at least one antibody and/or antigen-binding fragment thereof is administered to the feline at least once a week (e.g., at least once a day). In some embodiments of any of the methods described herein, the administering does not result in detrimental immunosuppression in the feline.

In any of the methods described herein, the retroviral infection is feline immunodeficiency virus (FIV) or feline leukemia virus (FELV). In some embodiments of any of the methods described herein, the retroviral virion is feline immunodeficiency virus (FIV) or feline leukemia virus (FELV).

Also provided herein are methods of using at least one antibody or antigen-binding fragment thereof that specifically binds to CD11a and/or CD18 (e.g., any of the exemplary antibodies or antibody fragments described herein) in the manufacture of a medicament for treating retrovirus infection in a feline, reducing retrovirus virion entry into a feline cell or retrovirus virion budding from a feline cell in a feline, and/or reducing syncytium transmission in a feline.

Also provided herein are antibodies or antigen-binding fragments thereof that specifically bind to CD11a and/or CD18 for use in treating retrovirus infection in a feline, reducing retrovirus virion entry into a feline cell or retrovirus virion budding from a feline cell in a feline, and/or reducing syncytium transmission in a feline.

Also provided herein are methods of using at least one small molecule that decreases LFA-1 binding to ICAM-1 (e.g., any of the small molecules that decrease LFA-1 binding to ICAM-1 described herein) in the manufacture of a medicament for treating retrovirus infection in a feline, reducing retrovirus virion entry into a feline cell or retrovirus virion budding from a feline cell in a feline, and/or reducing syncytium transmission in a feline.

Also provided herein are small molecules that decrease LFA-1 binding to ICAM-1 for use in treating retrovirus infection in a feline, reducing retrovirus virion entry into a feline cell or retrovirus virion budding from a feline cell in a feline, and/or reducing syncytium transmission in a feline.

Also provided herein are methods of using at least one antibody or antigen-binding fragment thereof that specifically binds to ICAM-1 (e.g., any of the exemplary antibodies or antigen-binding fragments thereof that specifically bind to ICAM-1 described herein) in the manufacture of a medicament for treating retrovirus infection in a feline, reducing retrovirus virion entry into a feline cell or retrovirus virion budding from a feline cell in a feline, and/or reducing syncytium transmission in a feline.

Also provided herein are antibodies or antigen-binding fragments thereof that specifically bind to ICAM-1 for use in treating retrovirus infection in a feline, reducing retrovirus virion entry into a feline cell or retrovirus virion budding from a feline cell in a feline, and/or reducing syncytium transmission in a feline.

By the term "retrovirus infection" or "retrovirus infection in a feline" is meant a disease in a feline where the causative agent is a retrovirus. Non-limiting examples of feline retroviruses are described herein.

By the term "lymphocyte function associated antigen-1" or "LFA-1" is meant a heterodimer of CD11a and CD18. LFA-1 plays a role in lymphocyte adhesion and activation leading to a normal immune response. Intercellular adhesion molecules (ICAMs)-1, -2, and -3 are ligands for LFA-1 expressed in the endothelium, leukocytes, and other cell types. As used herein, CD11a, CD18, and LFA-1 refer to feline CD11a, feline CD18, and feline LFA-1.

By the term "intracellular adhesion molecule-1" or "ICAM-1" is meant a cell surface adhesion receptor that is a member of the immunoglobulin protein super-family. ICAM-1 is expressed on a variety of hematopoietic and non-hematopoietic cells and is up-regulated at sites of inflammation by a variety of inflammatory mediators. ICAM-1 binds to several different cellular receptors, including LFA-1. As used herein, ICAM-1 refers to feline ICAM-1.

By the term "small molecule" is meant any small organic (e.g., peptides, nucleotides, sugars, and/or lipids), small inorganic molecules (e.g., metal complexes), or small organic/inorganic complexes (e.g., metal/protein complexes). In some embodiments, the small molecule can bind directly to CD11a and/or CD18 (bind to CD11a, CD18, or both CD11a and CD18), or ICAM-1. In some embodiments, the small molecule can bind indirectly to CD11a and/or CD18 or ICAM-1. In some embodiments, the small molecule can prevent or decrease LFA-1 binding to ICAM-1.

By the term "antibody" is meant any immunoglobulin or antibody (e.g., human, feline, mouse, cartilaginous fish, or camelid antibodies), and any derivative or conjugate thereof, that specifically binds to an antigen. A wide variety of antibodies are known by those skilled in the art. Non-limiting examples of antibodies include: monoclonal antibodies (e.g., including full-length antibodies), polyclonal antibodies, multi-specific antibodies (e.g., bi-specific antibodies), single-chain antibodies (e.g., single-domain antibodies, camelid antibodies, and cartilaginous fish antibodies), chimeric antibodies, feline antibodies, and felinized antibodies. The term antibody also includes antibody derivatives and conjugates (e.g., an antibody conjugated to a stabilizing protein, a detectable moiety, or a therapeutic agent).

By the term "antigen-binding fragment" is meant any portion of a full-length antibody that contains at least one of a variable domain (e.g., a variable domain of a mammalian (e.g., feline, human, or mouse) heavy or light chain immunoglobulin), a camelid variable antigen-binding domain (VHH), and a cartilaginous fish immunoglobulin new antigen receptor (Ig-NAR) domain) that is capable of specifically binding to an antigen. Non-limiting examples of antibody fragments include Fab, Fab', F(ab')$_2$, and Fv fragments, diabodies, linear antibodies, and multi-specific antibodies formed from antibody fragments. Additional antibody fragments containing at least one camelid VHH domain or at least one cartilaginous fish Ig-NAR domain include minibodies, micro-antibodies, subnano-antibodies, and nano-antibodies, and any of the other forms of antibodies described in U.S. Patent Application Publication No. 2010/0092470.

By the phrase "reduces LFA-1 binding to ICAM-1" is meant a statistically significant decrease (e.g., a detectable decrease, e.g., at least 10%, 15%, 20%, 25%, 30%, 35%, 40%, 45%, 50%, 55%, 60%, 65%, 70%, 75%, 80%, 85%, 90%, or 95% decrease) in the binding of LFA-1 to ICAM-1. The reduction in binding of LFA-1 binding to ICAM-1 can be compared to the amount of binding observed in the absence of treatment (e.g., in the absence of any agent as described herein, e.g., an antibody, antigen-binding fragment of an antibody, or small molecule). The binding of LFA-1 to ICAM-1 may be determined, for example, using in vitro cell culture assays or in vitro protein assays using purified proteins (e.g., BioCore technology) or cell lysates. Additional methods for determining binding of LFA-1 to ICAM-1 are known in the art. As used throughout the specification and claims, the phrase "LFA-1 binding to ICAM-1" and "ICAM-1 binding to LFA-1" is used interchangeably.

By the term "retrovirus virion" is meant a single infectious particle of a retrovirus (e.g., a feline retrovirus). A retroviral virion can contain an envelope derived from the plasma membrane of the host feline cell. Retroviral virions contain structural proteins that form a capsid that encloses a nucleic acid encoding the retroviral genome. As is known in the art, the structure of a retroviral virion and its components can vary between different feline retroviruses. In some embodiments, the retroviral virion can contain or present on its surface at least one of CD11a, CD18, or ICAM-1. The CD11a and CD18 present on the surface of a retroviral virion can form LFA-1 (a heterodimer of CD11a and CD18). The CD11a, CD18, or ICAM-1 contained or presented on the surface of the retroviral virion can contribute or play an active role in the entry (e.g., fusion) of the retroviral virion into a feline cell (e.g., a non-infected feline cell) or the budding or release of a retroviral virion into the extracellular space from an infected feline cell.

By the term "syncytium" is meant a large cell-like structure that contains cytoplasm, at least two nuclei, and an infectious retrovirus. A syncytium can express on its surface (plasma membrane) at least one of CD11a, CD18, or ICAM-1. CD11a and CD18 on the surface of a syncytium may form LFA-1 (a heterodimer of CD11a and CD18). The CD11a, CD18, or ICAM-1 present on the surface of the syncytium can contribute or play an active role in the fusion of the syncytium with a feline cell (e.g., a non-infected feline cell). The fusion (transient or permanent fusion) of a syncytium with a non-infected feline cell can promote the transmission of a retrovirus.

By the term "syncytium transmission" is meant the transfer of an infectious retrovirus from a syncytium to a non-infected feline cell that is mediated by fusion (e.g., transient or permanent fusion) of a syncytium with a non-infected feline cell. In some non-limiting embodiments, syncytium transmission can result in the transfer of a retroviral virion or capsid to a non-infected feline cell. A syncytium can fuse (e.g., transiently or permanently) with the plasma membrane of a non-infected target cell. Syncytial fusion with a non-infected target cell can be measured using any of the methods known in the art, including microscopic studies. A decrease in syncytium transmission in a feline can be detected by observing a reduction or a delay in the onset of retrovirus-induced dementia in a feline.

By the term "budding" is meant the release of a retroviral virion from an infected host cell that includes the step of enveloping a retroviral capsid in the plasma membrane of the infected host cell.

By the term "entry" is meant the natural introduction of at least one retroviral virion into a non-infected feline cell. Entry of a retroviral virion into a non-infected feline cell can include the step of fusion of a retroviral envelope (enclosing the retroviral capsid) with the plasma membrane of a non-infected feline cell. Retroviral virion entry can be measured using any of the methods known in the art, including microscopic studies.

By the term "feline antibody" is meant an antibody that is encoded by a nucleic acid (e.g., rearranged feline immunoglobulin heavy or light chain locus) present in the genome of a feline. In some embodiments, a feline antibody is produced by a feline or in a feline cell culture (e.g., feline hybridoma cells). In some embodiments, a feline antibody is produced in a non-feline cell (e.g., a mouse or human cell line). In some embodiments, a feline antibody is produced in a bacterial or yeast cell.

By the term "felinized antibody" is meant a feline antibody which contains minimal sequence derived from non-feline (e.g., mouse or human) immunoglobulin. In non-limiting examples, felinized antibodies are feline antibodies (recipient antibody) in which hypervariable region residues of the recipient antibody are replaced by hypervariable region residues from a non-feline species antibody (donor antibody), e.g., mouse, rat, rabbit, or human antibody having the desired specificity, affinity, and capacity. In some embodiments, the Fv framework residues of the feline immunoglobulin are replaced by corresponding non-feline residues. In some embodiments, felinized antibodies may contain residues which are not found in the recipient antibody or in the donor antibody. These modifications can be made to further refine antibody performance.

In some embodiments, the felinized antibody will contain substantially all of at least one, and typically two, variable domains, in which all or substantially all of the hypervariable loops (complementary determining regions) correspond to those of a non-feline immunoglobulin and all or substantially all of the framework regions are those of a feline immunoglobulin sequence. The felinized antibody can also contain at least a portion of an immunoglobulin constant region (Fc), typically, that of a feline immunoglobulin. Felinized antibodies can be produced by molecular biology methods known in the art. Non-limiting examples of methods for generating felinized antibodies are described herein.

By the term "single-chain antibody" is meant a single polypeptide that contains at least one variable binding domain (e.g., a variable domain of a mammalian heavy or light chain immunoglobulin, a camelid variable antigen-binding domain (VHH), or a cartilaginous fish (e.g., shark) immunoglobulin new antigen receptor (Ig-NAR) domain) that is capable of specifically binding to an antigen. Non-limiting examples of single-chain antibodies are described herein, and include single-domain antibodies (described herein).

By the term "single-domain antibody" is meant a polypeptide that contains one camelid variable antigen-binding domain (VHH) or at least one cartilaginous fish (e.g., shark) immunoglobulin new antigen receptor (Ig-NAR) domain that is capable of specifically binding to an antigen. Non-limiting examples of single-domain antibodies are described herein and are known in the art (see, for example, the antibodies described in U.S. Patent Publication No. 2010/0092470).

An antibody or antigen-binding fragment thereof "specifically binds" to a particular antigen, e.g., CD11a and/or CD18 (an epitope on CD11a, CD18, or an epitope that is formed by both CD11a and CD18), or ICAM-1, when it binds to that antigen, but recognizes and binds to a lesser extent (e.g., does not recognize and bind) to other molecules in a sample. In some embodiments, an antibody or an antigen-binding fragment thereof selectively binds to an epitope with an affinity ($K_D$) equal to or less than $1\times10^{-7}$ M (e.g., less than $1\times10^{-8}$ M or less than $1\times10^{-9}$ M) in phosphate buffered saline. The ability of an agent or molecule to specifically bind a second agent or molecule may be determined using any of the methods known in the art or those methods described herein.

By the phrase "decrease in the severity, frequency, or duration of at least one symptom" is meant a detectable or observable decrease in the intensity or clinical scoring of at least one symptom of a retroviral infection in a feline, a detectable or observable decrease in the recurrence of at least one symptom of a retroviral infection in a feline, or a detectable or observable decrease in the duration of at least one symptom of a retroviral infection in a feline. Symptoms of a retroviral infection in a feline may be detected, observed, or scored by a veterinary professional or any other individual (e.g., an owner of a domestic feline). A decrease in the severity, frequency, or duration of at least one symptom of a retroviral infection in a feline receiving a treatment (e.g., administered at least one of the agents described herein) may be compared to the severity, frequency, or duration of at least one symptom of a retroviral infection in a control feline (e.g., a feline having the same retroviral infection not receiving treatment or the same feline prior to treatment).

By the term "symptom of retroviral infection" is meant any observable or detectable physiological event that is significantly correlated with a retroviral infection in a feline. A symptom of retroviral infection may be observed by a veterinary professional or a symptom of retroviral infection may be detected by laboratory testing. Non-limiting examples of symptoms of retroviral infection in a feline include: decreased levels of $CD4^+$ T-cells (e.g., relative to a control feline or the same feline prior to infection), decreased ratio of $CD4^+$ T-cells to $CD8^+$ T-cells (e.g., relative to a control feline or the same feline prior to infection), decreased total white cell count (e.g., relative to a control feline or the same feline prior to infection), depression, lack of appetite, discharge from eyes and nose, fever, still and painful joints and muscles, difficulty breathing, sores in the mouth or on the lips, tongue, feet, or nose, weight loss, diarrhea, enlarged lymph nodes, skin infection, bladder infection, upper respiratory infection, seizures, vomiting, bloody diarrhea, weakness, conjunctivitis, stomatitis, odontoclasia, periodontitis, gingivitis, dementia, rhinitis, pneumonitis, enteritis, and dermatitis. Another symptom of a retroviral infection is uncontrolled proliferation of blood cells (feline leukemia). Additional symptoms of retroviral infection in a feline are described herein and are known in the art.

By the term "lovastatin derivative" is meant a modified lovastatin (a modified form of (1S,3R,7S,8S,8aR)-8-{2-[(2R,4R)-4-hydroxy-6-oxooxan-2-yl]ethyl}-3,7-dimethyl-1,2,3,7,8,8a-hexahydronaphthalen-1-yl (2S)-2-methylbutanoate) that has one or more of the following activities: ability to bind (e.g., $K_D$ equal to or less than $1 \times 10^{-6}$ M) to CD11a, CD18, ICAM-1, or both CD11a and CD18, or the ability to decrease binding of LFA-1 to ICAM-1. Non-limiting examples of lovastatin derivatives are described herein. Additional lovastatin derivatives are known in the art.

By the term "simvastatin derivative" is meant a modified simvaststin (a modified form of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 2,2-dimethylbutanoate) that has one or more of the following activities: ability to bind to CD11a, CD18, ICAM-1, or both CD11a and CD18 (e.g., $K_D$ equal to or less than $1 \times 10^{-6}$M), or the ability to decrease binding of LFA-1 to ICAM-1. Non-limiting examples of simvastatin derivatives are described herein. Additional examples of simvastatin derivatives are known in the art.

By the term "complementary determining region" or "CDR" is meant a region within an immunoglobulin (heavy or light chain immunoglobulin) that forms part of an antigen-binding site in an antibody or antigen-binding fragment thereof. As is known in the art, a heavy chain immunoglobulin contains three CDRs: CDR1, CDR2, and CDR3, respectively, and a light chain immunogloblun contains three CDRs: CDR1, CDR2, and CDR3. In any antibody or antigen-binding fragment thereof, the three CDRs from the heavy chain immunoglobulin and the three CDRs from the light chain immunoglobulin together form an antigen-binding site in the antibody or antigen-binding fragment thereof. The Kabat Database is one system used in the art to number CDR sequences present in a light chain immunoglobulin or a heavy chain immunoglobulin.

By the term "feline" is meant any mammal belonging to the family Felidae. Non-limiting examples of felines include domestic cats, feral cats, jaguars, lions, and tigers.

By the term "non-aromatic" refers to carbocycle or heterocycle rings that do not have the properties of aromaticity. Aromaticity requires a ring to be planar, have $\Xi$-orbitals that are perpendicular to the plane of the ring at each ring atom and satisfy the Huckel rule, where the number of $\Xi$ electrons in the ring is (4n+2) and n is an integer (i.e., the number of $\Xi$ electrons is 2, 6, 10, or 14). Non-aromatic rings do not satisfy one or all of these criteria for aromaticity.

By the term "alkoxy" is meant O-alkyl, O-alkenyl, or an O-alkynyl group. Non-limiting examples of alkoxy groups include methoxy, ethoxy, propoxy, butoxy, i-butoxy, s-butoxy, t-butoxy, pentyloxy, and hexyloxy.

By the term "amino" is meant a primary ($-NH_2$), secondary ($-NHR$), tertiary ($-N(R)_2$), or quaternary ($-N^+(R)_4$) amine, where R is a hydrocarbon chain, a hydroxy, a carbocycle, a heterocycle, or a hydrocarbon substituted with a carbocycle or a heterocycle.

By the term "carboxyl" is meant a free acid —COOH, as well as esters thereof, such as alkyl, aryl, and aralkyl esters. In some embodiments, the esters are methyl, ethyl, propyl, butyl, i-butyl, s-butyl, and t-butyl esters.

By the term "carbocycle" is meant a mono-, bi-, or tri-cyclic carbon ring or ring system having 4-16 members (including bridged members) which is saturated, unsaturated, or partially unsaturated, including aromatic (aryl) ring systems (unless specified as non-aromatic). Non-limiting examples of non-aromatic carbocyclic rings are cyclopropyl, cyclopropentyl, cyclobutyl, cyclobutenyl, cyclopentyl, cyclopentenyl, cyclohexyl, and cyclohexenyl. Non-limiting examples of aromatic carbocyclic rings are phenyl and naphthyl.

By the term "heterocycle" is meant a mono-, bi-, or tri-cyclic ring system having 5-16 members, where at least one ring atom is a heteroatom (i.e., N, O, and S, as well as SO or $SO_2$). The ring system is saturated, unsaturated, or partially unsaturated and may be aromatic (unless specified as non-aromatic). Non-limiting examples of heterocycles are piperidine, piperazine, pyridine, pyrazine, pyrimidine, pyridazine, morpholine, pyran, pyrole, furan, thiophene (thienyl), imidazole, pyrazole, thiazole, isothiazole, dithiazole, oxazole, isoxazole, dioxazole, thiadiazole, oxadiazole, tetrazole, triazole, thiatriazole, oxatriazole, thiadiazole, and purine and benzofused derivatives thereof.

By the term "hydrocarbon chain" is meant a saturated, unsaturated, linear, or branched carbon chain (i.e., alkyl, alkenyl, or alkynyl). Non-limiting examples of hydrocarbon chains contain 1-12 carbon atoms, 1-6 carbon atoms, or 1-4 carbon atoms (e.g., methyl, ethyl, propyl, butyl, or alkyl).

By the phrase "optionally substituted with" is meant to mean, unless otherwise stated, that one or more of the specified substituents is covalently attached to the substituted moiety. When there is more than one substituent, the substituents can be the same or different groups.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 6 shows the sequence information corresponding to SEQ. ID NO: 1, or >7299 (Felinized HC 1).

FIG. 7 shows the sequence information corresponding to SEQ. ID NO: 2, or >7300 (Felinized HC 2).

FIG. 8 shows the sequence information corresponding to SEQ. ID NO: 3, or >7301 (Felinized HC 3).

FIG. 9 shows the sequence information corresponding to SEQ. ID NO: 4, or >7302 (Felinized LC 1).

FIG. 10 shows the sequence information corresponding to SEQ. ID NO: 5, or >7303 (Felinized LC 2).

FIG. 11 shows the sequence information corresponding to SEQ. ID NO: 6, or >7304 (Felinized LC 3)

FIG. 12 shows the sequence information corresponding to SEQ. ID NO: 7, or Feline.

Figure 1A:
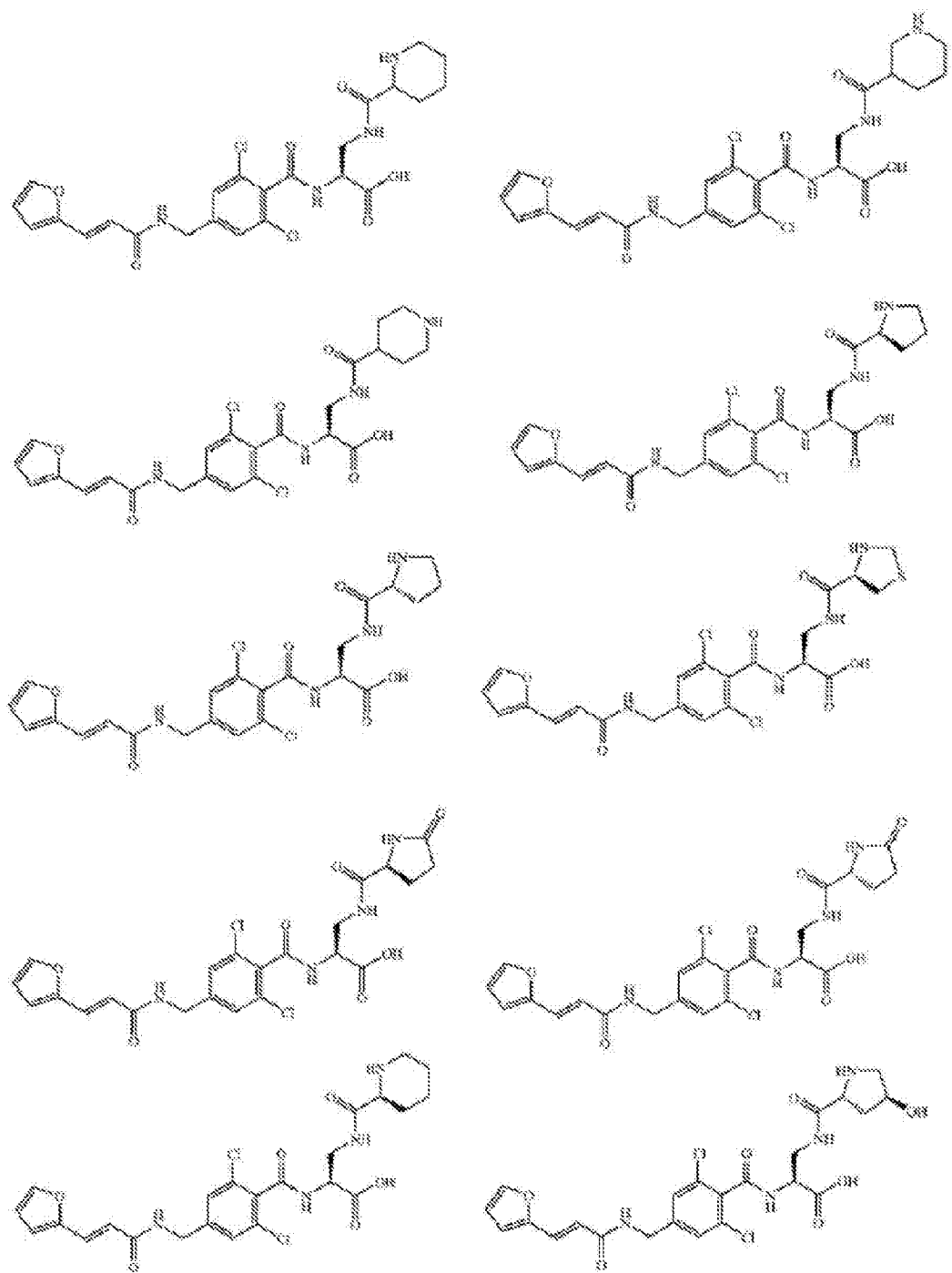
FIGS. 1A-F shows non-limiting examples of small molecules of Formula I that can be used in any of the methods described herein.
Figure 1B:
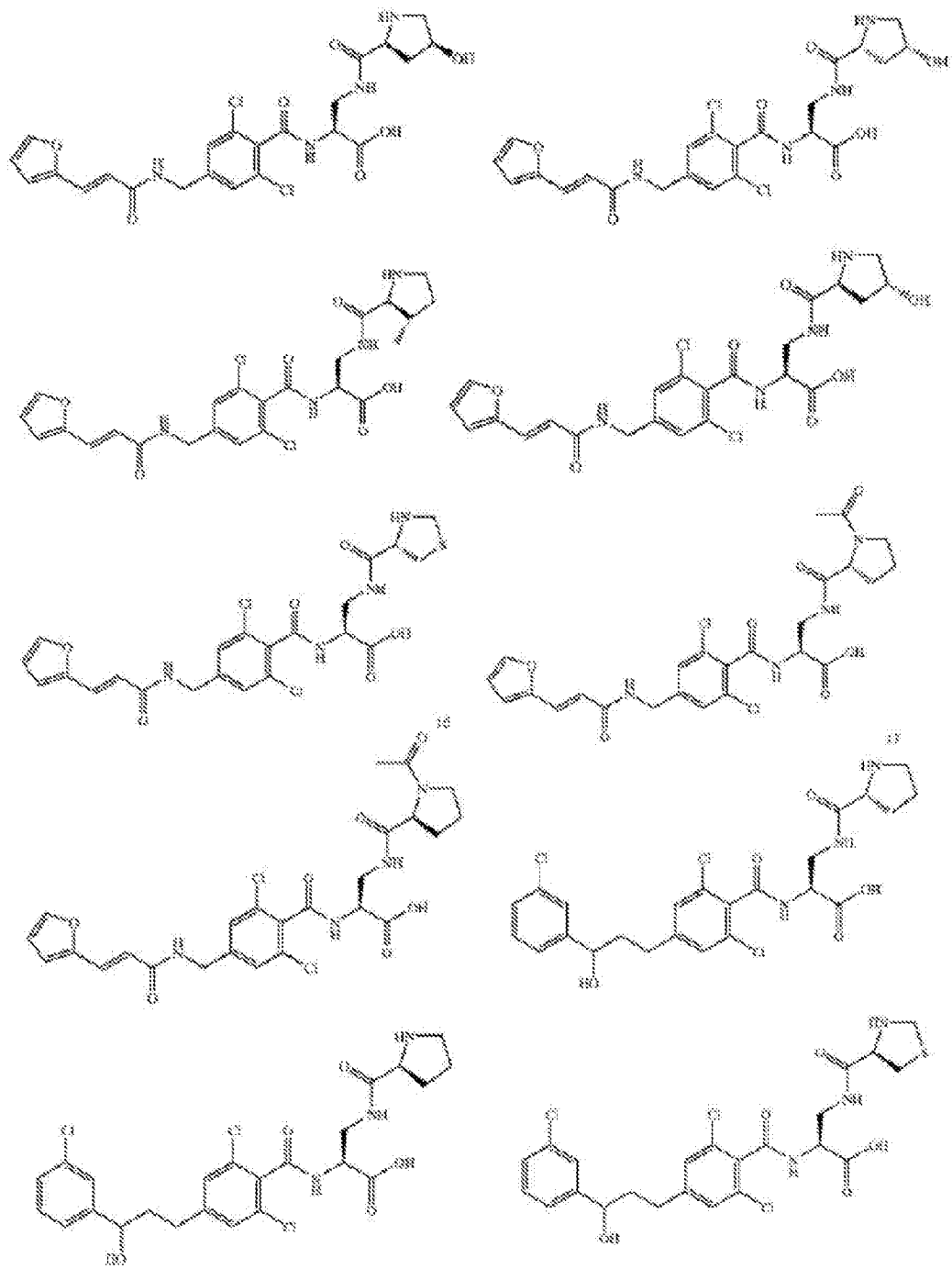
Figure 1C:
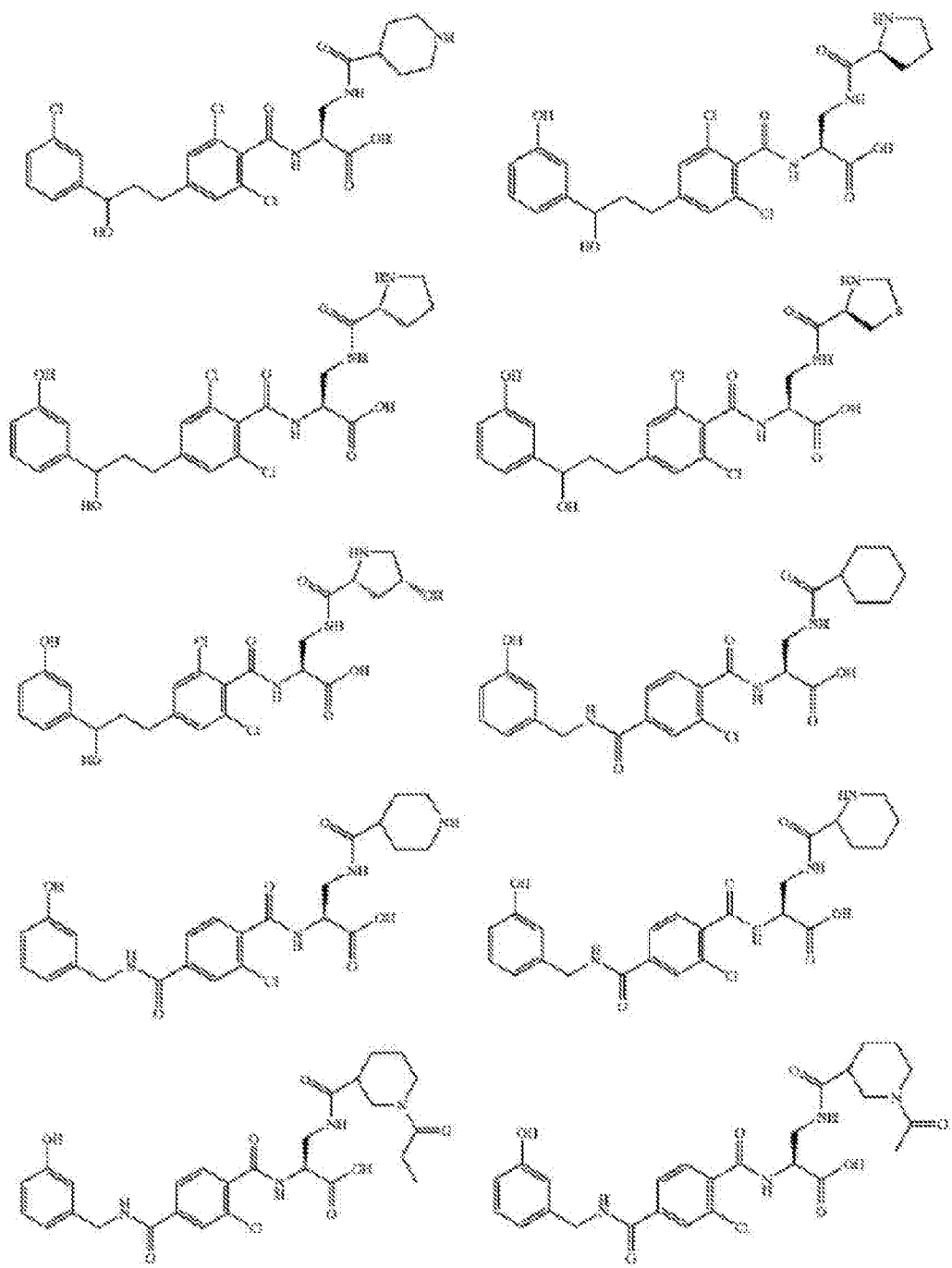
Figure 1D:
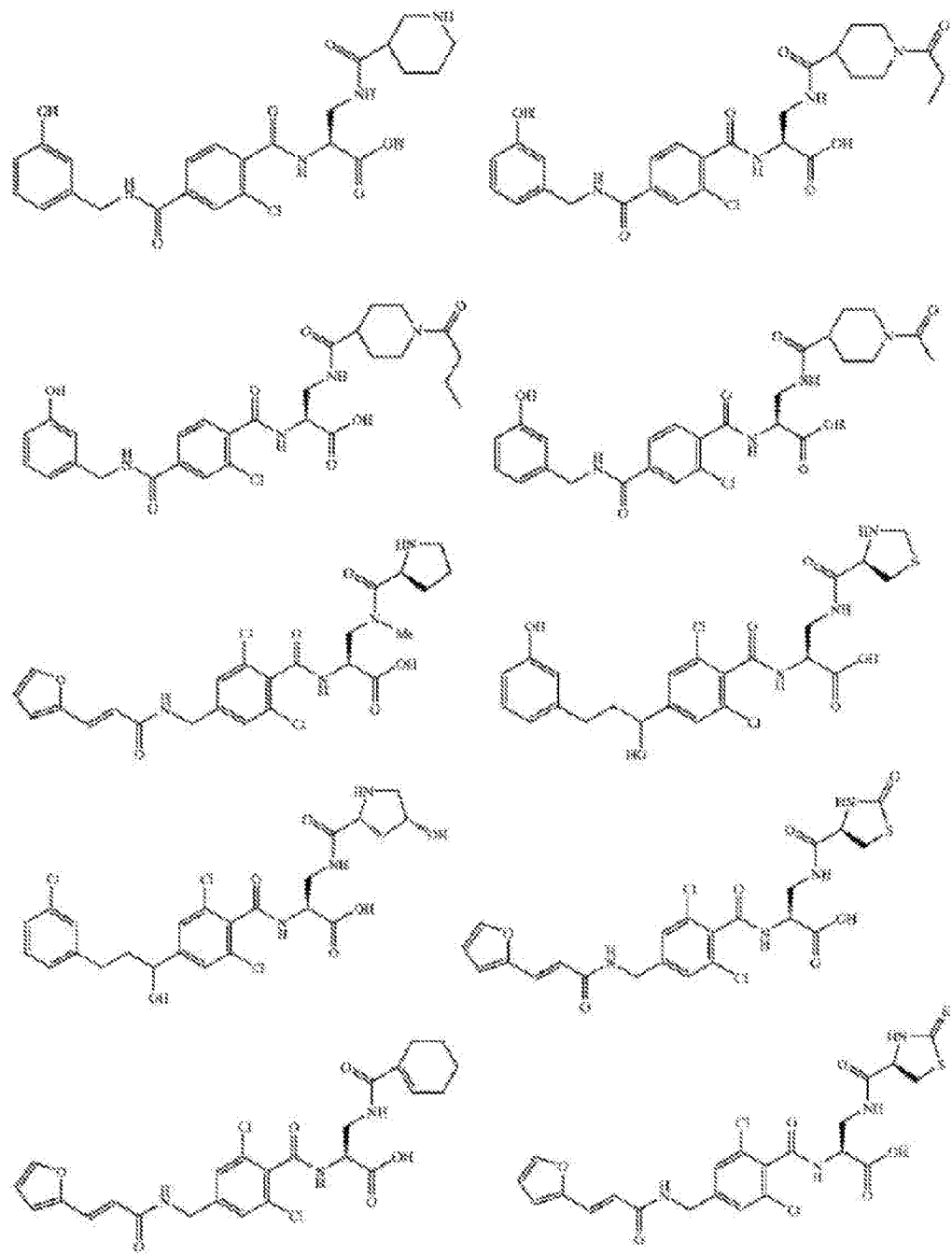
Figure 1E:
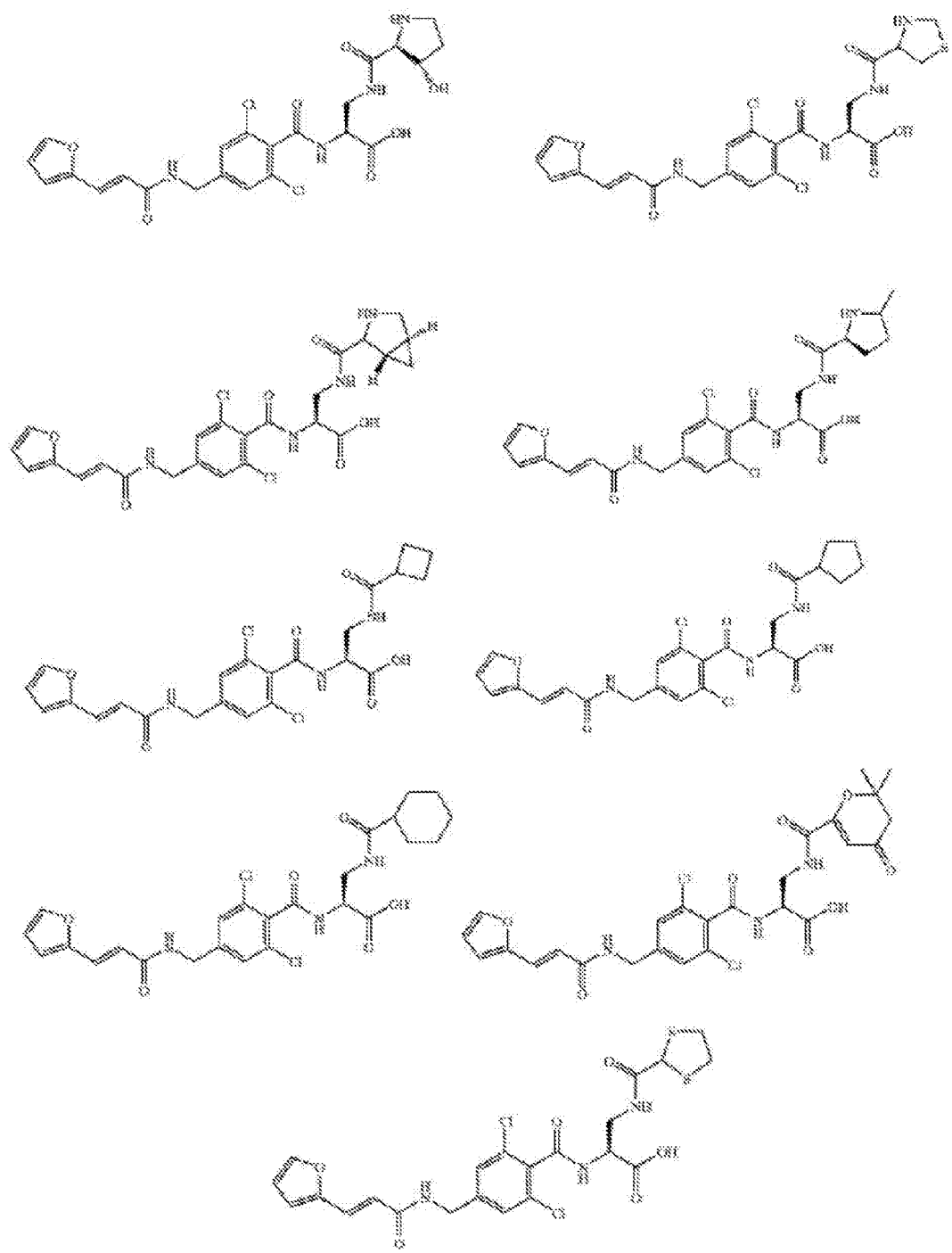
Figure 1F:
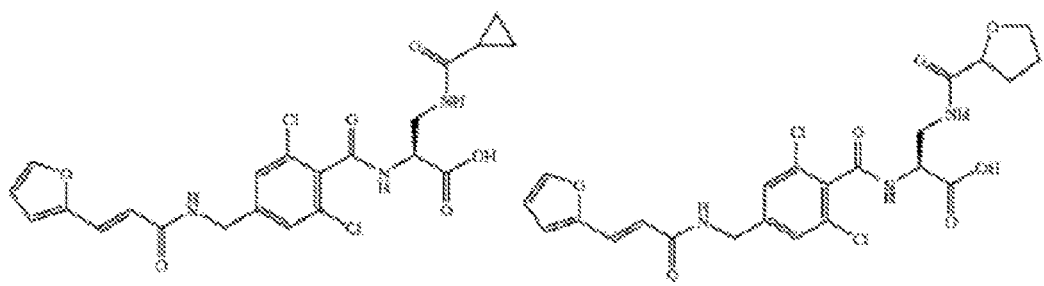

IgG1 heavy chain constant region.

FIG. 13 shows the sequence information corresponding to SEQ. ID NO: 8, or Feline kappa light chain constant region.

DETAILED DESCRIPTION

Provided herein are felinized antibodies and methods and compositions for treating or reducing retroviral infections in felines.
Feline Retroviral Diseases The feline retroviruses feline immunodeficiency virus (FIV) and feline leukemia virus (FELV) cause disease in felines. FIV is a member of the lentivirus subfamily of retroviruses. It appears to have been widely distributed worldwide since the 1960s. There are 5 FIV subtypes (clades A to E) and they all are infectious to a variety of susceptible wild and domestic feline species. In the U.S.A., the prevalence of HIV infection for domestic cats is estimated to be 1-4%, and this number is larger in the feral cat population.

FIV has a primary tropism for lymphocytes and gradually destroys sub-populations of T-lymphocytes. This cytopathic effect causes a progressive loss of $CD4^+$ T-cells, a decrease in the $CD4^+$ T-cell/$CD8^+$ T-cell ratio, and the eventual loss of measurable levels of $CD8^+$ T-cells in the late stages of infection. Cell-mediated immunity is impaired to a greater extent than antibody-mediated immunity. In addition, impaired production and dysregulation of various cytokines plays a role in pathogenesis of the disease. Antiretroviral drugs are too toxic for felines, leaving virtually no alternative for treating FIV.

FELV is an RNA retrovirus and was described in 1964 (Jarrett et al., Nature 202:566, 1964). FELV and FIV are in the same viral family. Four subgroups of FELV exist: A, B, C, and T. Approximately 0.5% of domestic felines are persistently infected with FELV, but many more domestic felines (>35%) have specific IgG antibodies. Transmission of FELV is mainly through saliva and friendly behaviors, such as sharing feeding bowls and mutual grooming.

FELV causes uncontrolled proliferation of blood cells in felines. Additional symptoms of FELV in felines include infections of the skin, bladder, and respiratory tract, oral disease, seizures, lymphadenopathy, skin lesions, fatigue, fever, weight loss, stomatitis, gingivitis, litter box avoidance, pancytopenia, poor grooming, reoccurring bacterial and viral illnesses, anemia, diarrhea, and jaundice.

Feline retroviral infection can be diagnosed by a skilled veterinary professional (e.g., a veterinarian, a veterinarian assistant, a veterinary technician, or a lab technician). For example, a feline retroviral infection may be determined by the observation of one or more symptoms of a retroviral infection in a feline. Non-limiting examples of symptoms of retroviral infection in a feline include, in addition to those listed above: decreased levels of $CD4^+$ T-cells (e.g., relative to a control feline or the same feline prior to infection), decreased ratio of $CD4^+$ T-cells to $CD8^+$ T-cells (e.g., relative to a control feline or the same feline prior to infection), decreased total white cell count (e.g., relative to a control feline or the same feline prior to infection), depression, lack of appetite, discharge from eyes and nose, fever, still and painful joints and muscles, difficulty breathing, sores in the mouth or on the lips, tongue, feet, or nose, weight loss, diarrhea, enlarged lymph nodes, skin infection, bladder infection, upper respiratory infection, seizures, dementia, vomiting, bloody diarrhea, weakness, conjunctivitis, stomatitis, odontoclasia, periodontitis, gingivitis, rhinitis, pneumonitis, enteritis, and dermatitis. Another symptom of a feline retroviral infection is dementia. A feline retroviral disease can also be diagnosed using commercially available diagnostic kits (e.g., an assay that measures antibody titers in a feline that bind to the retrovirus (e.g., bind to a retroviral protein), an assay that measures the presence of proteins present in the retrovirus, or an assay that measures the presence of a nucleic acid present in the retrovirus). For example, diagnostic kits for the diagnosis of FIV or FELV in a feline are commercially available from Anigen Rapid (FIV Ab/FeLV Ag Test Kit) and Idexx (SNAP® Feline Triplet Test). Another diagnostic kit for the diagnosis of FIV is commercially available from Vita-Tech Laboratories (Feline Immunodeficiency Virus (FIV) DNA Confirmatory Test).

A skilled veterinary professional can determine the effectiveness of treatment of a retroviral infection in a feline by monitoring the number of symptoms or the severity, frequency, and/or duration of one or more symptoms of a retrovirus infection in a feline. For example, a useful treatment may result in a statistically significant or observable decrease in the severity, duration, or frequency of one or more (e.g., one, two, three, four, or five) symptoms in a feline having a retroviral infection. A useful treatment may also result in a decrease of retroviral titers in the feline (e.g., a decrease in retroviral titers in a specific biological fluid of the feline, e.g., serum, blood, lung fluid, nasal fluid, intestinal fluid, or gastric fluid). A useful treatment of FIV or FELV can also result in one or more (e.g., one, two, three, four, or five) of: an increase in $CD4^+$ T-cell level (e.g., relative to a control feline having FIV or FELV, but not receiving treatment or the same feline prior to treatment), an increase in the $CD4^+$ T-cell to $CD8^+$ T-cell ratio (e.g., relative to a control feline having FIV or FELV, but not receiving treatment or the same feline prior to treatment), a decrease in $CD8^+$ T-cell-mediated killing of $CD4^+$ T-cells (e.g., relative to a control feline having FIV or FELV, but not receiving treatment or the same feline prior to treatment), a decrease retroviral virion or syncytium fusion with non-infected feline cells (e.g., relative to a control feline having FIV or FELV, but not receiving treatment or the same feline prior to treatment), a decrease in syncytium transmission in a feline (e.g., relative to the amount of syncytium transmission in a feline without FIV or FELV, or in the same feline prior to treatment), and a decrease in the development or rate of onset of retrovirus-induced dementia (e.g., relative to a control feline having FIV, but not receiving treatment or the same feline prior to treatment). A skilled veterinary professional may adjust the treatment (e.g., dosage of agents and/or frequency or duration of administration of agents) based on the assessment of the effectiveness of the retroviral infection treatment as described herein.

LFA-1 and ICAM-1

Lymphocyte function-associated antigen-1 (LFA-1) is a cell surface heterodimer of CD11a and CD18 proteins that is present on a variety of cells, including T-cells, B-cells, macrophages, and neutrophils. LFA-1 is involved in the recruitment of cells to the site of infection. LFA-1 also binds to ICAM-1 on antigen-presenting cells, and functions as an adhesion molecule. In any of the embodiments described herein, an antibody or an antigen-binding fragment thereof can bind to CD11a or CD18, or may bind to an epitope formed by both CD11a and CD18. In any of the embodiments described herein, at least one small molecule can bind to CD11a or CD18, or both CD11a and CD18.

Intercellular adhesion molecule 1 (ICAM-1), also known as cluster of differentiation 54 (CD54), is a cell surface glycoprotein that is typically expressed on endothelial cells and cells of the immune system (e.g., antigen-presenting cells). As noted above, ICAM-1 binds to LFA-1.

Provided are methods that treat or reduce (e.g., significantly reduce) the likelihood of developing a retroviral infection in a feline. These methods require administering to a feline at least one (e.g., one, two, three, or four) agent (e.g., a small molecule or antibody or antigen-binding fragment thereof) that specifically binds to CD11a and/or CD18 (specifically binds to CD11a, CD18, or an epitope formed by both CD11a and CD18), or ICAM-1, and/or prevents LFA-1 present in a retroviral virion or syncytium from binding to ICAM-1 expressed on the surface of a feline cell (e.g., a non-infected cell). In some embodiments, the at least one agent prevents LFA-1 present in a feline cell (e.g., a non-infected feline cell) from binding to ICAM-1 in a virion or syncytium.

During a retroviral infection in a feline, virions bud off from or are released from an infected host feline cell. Syncytia fuse (transiently or permanently) with non-infected feline cells. Retroviral virions incorporate cellular proteins (e.g., CD11a, CD18, or ICAM-1) expressed in feline cells during budding from the host cell. A syncytium incorporates cellular proteins (e.g., CD11a, CD18, or ICAM-1) expressed in a feline cell during fusion of the syncytium with a feline cell. CD11a and CD18 present in the virion or syncytium can form LFA-1 (a heterodimer of CD11a and CD18). CD11a, CD18, or ICAM-1 present in the virion or syncytium can aid or facilitate the binding and/or entry of the retroviral virion, or the binding and/or fusion of a syncytium with a non-infected target cell in the feline. In some embodiments, the binding, entry, and/or fusion is facilitated by LFA-1 present on the surface of a virion or syncytium binding to ICAM-1 present on the surface of a non-infected feline cell (e.g., directly or indirectly facilitating retroviral virion binding and/or entry, or syncytium binding and/or fusion with a non-infected feline cell). In some embodiments, the binding, entry, and/or fusion is facilitated by LFA-1 present on the surface of a non-infected feline cell binding to ICAM-1 present on the surface of a virion or syncytium (e.g., directly or indirectly facilitating retroviral virion binding and/or entry, or syncytium binding and/or fusion with a non-infected feline cell).

In any of the methods described herein and used throughout, LFA-1 or ICAM-1 can be found on the surface of a retroviral virion or syncytium or can be found in a feline cell (e.g., a non-infected feline cell).

Agents

Provided herein are methods of treating or reducing the likelihood of developing a retroviral infection that require the administration of at least one agent that prevents or decreases the binding of LFA-1 to ICAM-1.

Agents useful in the methods described herein include, without limitation, antibodies and antigen-binding fragments thereof, and small molecules. Non-limiting examples of antibodies and antigen-binding fragments thereof and small molecules that prevent or decrease the binding of LFA-1 to ICAM-1 are described herein. Additional agents useful for preventing or decreasing the binding of LFA-1 to ICAM-1 are known in the art. Additional agents useful in the methods described herein can be identified using the screening methods described herein. Two or more (e.g., two, three, four, or five) of the agents described herein can be administered to a feline in any combination without limitation.

Antibodies and Antigen-Binding Fragments Thereof

Agents useful in any of the methods described herein include antibodies and antigen-binding fragments thereof. In some embodiments, the antibodies and antigen-binding fragments thereof bind to an epitope on CD11a, CD18, or ICAM-1, or an epitope formed by both CD11a and CD18, that is present in or on the surface of a virion or syncytium or bind to an epitope on CD11a, CD18, or ICAM-1, or an epitope formed by both CD11a and CD18, that is present in or on the surface of a non-infected feline cell. In some embodiments, the antibodies and antigen-binding fragments thereof bind to an epitope on ICAM-1 (e.g., ICAM-1 present in or on the surface of a virion, syncytium, or non-infected feline cell).

In some embodiments, the antibody or antigen-binding fragment thereof specifically binds to (e.g., binds to an epitope present in) feline CD11a, CD18, ICAM-1, or an epitope formed by both CD11a and CD18. In some embodiments, the antibody or antigen-binding fragment thereof prevents or reduces the binding of a LFA-1 present in or on the surface of a virion or syncytium to ICAM-1 present in or on the surface of a feline cell (e.g. a non-infected feline cell). In some embodiments, the antibody or antigen-binding fragment thereof prevents or reduces the binding of a LFA-1 present in or on the surface of a non-infected feline cell to ICAM-1 present in or on the surface of a virion or syncytium. The prevention or reduction of binding of a LFA-1 to ICAM-1 can occur directly (the antibody or antigen-binding fragment thereof binds directly to CD11a, CD18, ICAM-1, or an epitope formed by both CD11a and CD18) or indirectly (the antibody or antigen-binding fragment thereof binds to a protein, lipid, and/or carbohydrate that directly binds to CD11a, CD18, ICAM-1, or both CD11a and CD18).

Methods for determining the ability of an antibody or antigen-binding fragment thereof to bind to a target protein (e.g., CD11a, CD18, ICAM-1, or an epitope formed by both CD11a and CD18) can be performed using methods known in the art. Non-limiting examples of such methods include competitive binding assays using antibodies known to bind the target protein (e.g., CD11a, CD18, ICAM-1, or an epitope formed by both CD11a and CD18), enzyme-linked immunosorbent assays, BioCoRE®, affinity columns, immunoblotting, or protein array technology. In some embodiments, the binding activity of the antibody or antigen-binding fragment thereof is determined by contacting a feline cell (e.g., a $CD8^+$ T-cell, a $CD4^+$ T-cell, a dendritic cell, a fibroblast, or an epithelial cell) with the antibody or antigen-binding fragment thereof. Additional methods for identifying agents (antibodies or antigen-binding fragments thereof) that bind to CD11a, CD18, ICAM-1, or an epitope formed by both CD11a and CD18 are described herein.

In some embodiments of any of the methods described herein, the antibody or antigen-binding fragment thereof binds to CD11a, CD18, ICAM-1, or an epitope formed by both CD11a and CD18 with an $K_D$ equal to or less than $1\times10^{-7}$M, a $K_D$ equal to or less than $1\times10^{-8}$M, a $K_D$ equal to or less than $5\times10^{-8}$ M, a $K_D$ equal to or less than $1\times10^{-9}$M, or a $K_D$ equal to or less than $5\times10^{-9}$ M under physiological conditions (e.g., phosphate buffered saline).

An antibody can be any immunoglobulin or antibody (including, for example, variants, derivatives, and conjugates thereof) that specifically binds an antigen, such as light or heavy chain immunoglobulin molecules and immunologically-active fragments of immunoglobulin molecules. An antibody can also be a single-chain antibody (e.g., a single-domain antibody), such as a single-chain camelid or cartilaginous fish (e.g., shark) antibody, or a single-chain antibody that contains at least one camelid variable antigen-binding domain (VHH) or at least one cartilaginous fish (e.g., shark) immunoglobulin new antigen receptor (Ig-NAR) domain (see, for example, the antibodies described in U.S. Patent Publication No. 2010/0092470). An antibody can be a whole antibody molecule or an antibody multimer.

Antibodies as referred to herein include variants (including derivatives) of antibodies, antibody multimers, and antibody fragments. Examples of antibodies include, but are not limited to: single-chain Fvs (sdFvs), single-domain antibodies (e.g., mini-antibodies, micro-antibodies, sub-nano-antibodies, and nano-antibodies, see for example, the antibodies described in U.S. Patent Application Publication No. 2010/0092470), Fab fragments, Fab' fragments, F(ab')$_2$, disulfide-linked Fvs (sdFvs), Fvs, and fragments containing, either a VL or a VH domain. The term "single chain Fv" or "scFv" as used herein refers to a polypeptide comprising at least one VL domain of antibody linked to at least one VH domain of an antibody.

Antibodies useful in the methods described herein include, but are not limited to, polyclonal, monoclonal, multispecific (e.g., bi-specific), feline, human, mouse, rabbit, or rat antibodies, chimeric antibodies (e.g., human-feline chimera, mouse-feline chimera, rat-feline chimera, or rabbit-feline chimera), single chain antibodies (e.g., single-domain antibodies), Fab fragments, F(ab') fragments, intracellularly-made antibodies (i.e., intrabodies), epitope-binding fragments of any of the above, and any of the other antibodies or antigen-binding fragments described herein. The antibodies or antigen-binding fragments thereof can be of any type (e.g., IgG, IgE, IgM, IgD, IgA, and IgY), class (e.g., $IgG_1$, $IgG_2$, $IgG_3$, $IgG_4$, $IgA_1$, and $IgA_2$) or subclass. In some embodiments, the antibody or antigen-binding fragment thereof is an $IgG_1$ antibody or fragment thereof. In other embodiments, the antibody or antigen-binding fragment thereof is an $IgG_4$ antibody or antigen-binding fragment thereof. Immunoglobulins may have both a heavy and light chain.

An isolated feline CD11a, CD18, ICAM-1, or LFA-1 (heterodimer of CD11a and CD18), or fragment thereof can be used as an immunogen to generate antibodies using standard techniques for polyclonal and monoclonal antibody preparation. For example, feline CD11a can be purified using the methods described in Shimojima et al. (*Microbes Infection* 5:1171-1176, 2003). In this method, feline CD11a is isolated by first cloning feline CD11a from a peripheral blood mononuclear cell (PBMC) cDNA library using the homologue cloning method using the polymerase chain reaction (Nishimura et al., *Immunogenetics* 50:369-370, 1999) and expressing the cDNA in insect cells using a recombinant baculovirus vector containing the cloned cDNA downstream of a polyhedrin promoter (Shimojima et al., *J. Vet. Med. Sci.* 59:467-469, 1997; and Shimojima et al., *Vet. Immunol. Immunopathol.* 61:17-23, 1998).

The full-length polypeptide or protein (e.g., CD11a, CD18, LFA-1, or ICAM-1) can be used or, alternatively, antigenic peptide fragments can be used as immunogens. The antigenic peptide of a protein comprises at least 8 (e.g., at least 10, 15, 20, or 30) amino acid residues of the amino acid sequence of the protein (e.g., CD11a, CD18, or ICAM-1) and encompasses an epitope of the protein such that an antibody raised against the peptide forms a specific immune complex with the protein.

An immunogen typically is used to prepare antibodies by immunizing a suitable subject (e.g., rabbit, goat, mouse, or other mammal). An appropriate immunogenic preparation can contain, for example, a recombinantly expressed or a chemically synthesized polypeptide. The preparation can further include an adjuvant, such as Freund's complete or incomplete adjuvant, or a similar immunostimulatory agent.

Polyclonal antibodies can be prepared as described above by immunizing a suitable subject with feline CD11a, CD18, ICAM-1, or LFA-1, or an antigenic peptide thereof, as an immunogen. The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler et al. (*Nature* 256:495-497, 1975), the human B cell hybridoma technique (Kozbor et al.,

*Immunol. Today* 4:72, 1983), the EBV-hybridoma technique (Cole et al., Monoclonal Antibodies and Cancer Therapy, Alan R. Liss, Inc., pp. 77-96, 1985), or trioma techniques. The technology for producing hybridomas is well known (see, generally, Current Protocols in Immunology, 1994, Coligan et al. (Eds.), John Wiley & Sons, Inc., New York, N.Y.). Hybridoma cells producing a monoclonal antibody are detected by screening the hybridoma culture supernatants for antibodies that bind the polypeptide of interest, e.g., using a standard ELISA assay.

As an alternative to preparing monoclonal antibody-secreting hybridomas, a monoclonal antibody directed against a polypeptide can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SurfZAP* Phage Display Kit, Catalog No. 240612). Additionally, examples of methods and reagents particularly amenable for use in generating and screening an antibody display library can be found in, for example, U.S. Pat. No. 5,223,409; WO 92/18619; WO 91/17271; WO 92/2079; WO 92/15679; WO 93/01288; WO 92/01047; WO 92/09690; WO 90/02809; Fuchs et al., *Bio/Technology* 9:1370-1372, 1991; Hay et al., *Hum. Antibod. Hybridomas* 3:81-85, 1992; Huse et al., *Science* 246:1275-1281, 1989; Griffiths et al., *EMBO J.* 12:725-734, 1993.

In some embodiments of any of the methods described herein, the antibodies or antigen-binding fragments are feline antibodies or felinized antibodies. In some embodiments, a felinized antibody is a feline antibody that has been engineered to contain at least one complementary determining region (CDR) present in a non-feline antibody (e.g., a human, rat, mouse, rabbit, or goat antibody). In some embodiments, a felinized antibody or fragment thereof can contain all three CDRs of a light chain of a mouse (e.g., the TS1/22 antibody) or human monoclonal antibody that specifically binds to CD11a, CD18, ICAM-1, or an epitope formed by both CD11a and CD18. In some embodiments, the felinized antibody or fragment thereof can contain all three CDRs of a heavy chain of a mouse (e.g., the TS1/22 antibody) or human monoclonal antibody that specifically binds to CD11a, CD18, ICAM-1, or an epitope formed by both CD11a and CD18. In some embodiments, the felinized antibody or fragment thereof can contain all three CDRs of a heavy chain and all three CDRs of a light chain of a mouse (e.g., the TS1/22 antibody) or human monoclonal antibody that specifically binds to CD11a, CD18, ICAM-1, or an epitope formed by both CD11a and CD18.

Antibodies of the invention may also include multimeric forms of antibodies. For example, antibodies of the invention may take the form of antibody dimers, trimers, or higher-order multimers of monomeric immunoglobulin molecules. Dimers of whole immunoglobulin molecules or of F(ab')$_2$ fragments are tetravalent, whereas dimers of Fab fragments or scFv molecules are bivalent. Individual monomers within an antibody multimer may be identical or different, i.e., they may be heteromeric or homomeric antibody multimers. For example, individual antibodies within a multimer may have the same or different binding specificities.

Multimerization of antibodies may be accomplished through natural aggregation of antibodies or through chemical or recombinant linking techniques known in the art. For example, some percentage of purified antibody preparations (e.g., purified IgG$_1$ molecules) spontaneously form protein aggregates containing antibody homodimers and other higher-order antibody multimers. Alternatively, antibody homodimers may be formed through chemical linkage techniques known in the art. For example, heterobifunctional crosslinking agents including, but not limited to, SMCC (succinimidyl 4-(maleimidomethyl)cyclohexane-1-carboxylate) and SATA (N-succinimidyl S-acethylthio-acetate) (available, for example, from Pierce Biotechnology, Inc. (Rockford, Ill.)) can be used to form antibody multimers. An exemplary protocol for the formation of antibody homodimers is given in Ghetie et al. (*Proc. Natl. Acad. Sci. U.S.A.* 94: 7509-7514, 1997). Antibody homodimers can be converted to Fab'$_2$ homodimers through digestion with pepsin. Another way to form antibody homodimers is through the use of the autophilic T15 peptide described in Zhao et al. (*J. Immunol.* 25:396-404, 2002).

Alternatively, antibodies can be made to multimerize through recombinant DNA techniques. IgM and IgA naturally form antibody multimers through the interaction with the mature J chain polypeptide. Non-IgA or non-IgM molecules, such as IgG molecules, can be engineered to contain the J chain interaction domain of IgA or IgM, thereby conferring the ability to form higher order multimers on the non-IgA or non-IgM molecules (see, for example, Chintalacharuvu et al., *Clin. Immunol.* 101:21-31, 2001, and Frigerio et al., *Plant Physiol.* 123:1483-1494, 2000). IgA dimers are naturally secreted into the lumen of mucosa-lined organs. This secretion is mediated through interaction of the J chain with the polymeric IgA receptor (pIgR) on epithelial cells. If secretion of an IgA form of an antibody (or of an antibody engineered to contain a J chain interaction domain) is not desired, it can be greatly reduced by expressing the antibody molecule in association with a mutant J chain that does not interact well with pIgR (Johansen et al., *J. Immunol.*, 167:5185-192, 2001). ScFv dimers can also be formed through recombinant techniques known in the art; an example of the construction of scFv dimers is given in Goel et al. (*Cancer Res.* 60:6964-71, 2000). Antibody multimers may be purified using any suitable method known in the art, including, but not limited to, size exclusion chromatography.

Any of the antibodies or antigen-binding fragments described herein may be conjugated to a stabilizing molecule (e.g., a molecule that increases the half-life of the antibody or antigen-binding fragment thereof in a feline or in solution). Non-limiting examples of stabilizing molecules include: a polymer (e.g., a polyethylene glycol) or a protein (e.g., serum albumin, such as feline serum albumin). Any of the antibodies or antigen-binding fragments described herein may be conjugated to a label (e.g., a fluorophore) or a therapeutic agent (e.g., a proteinaceous therapeutic agent).

Figure 2:
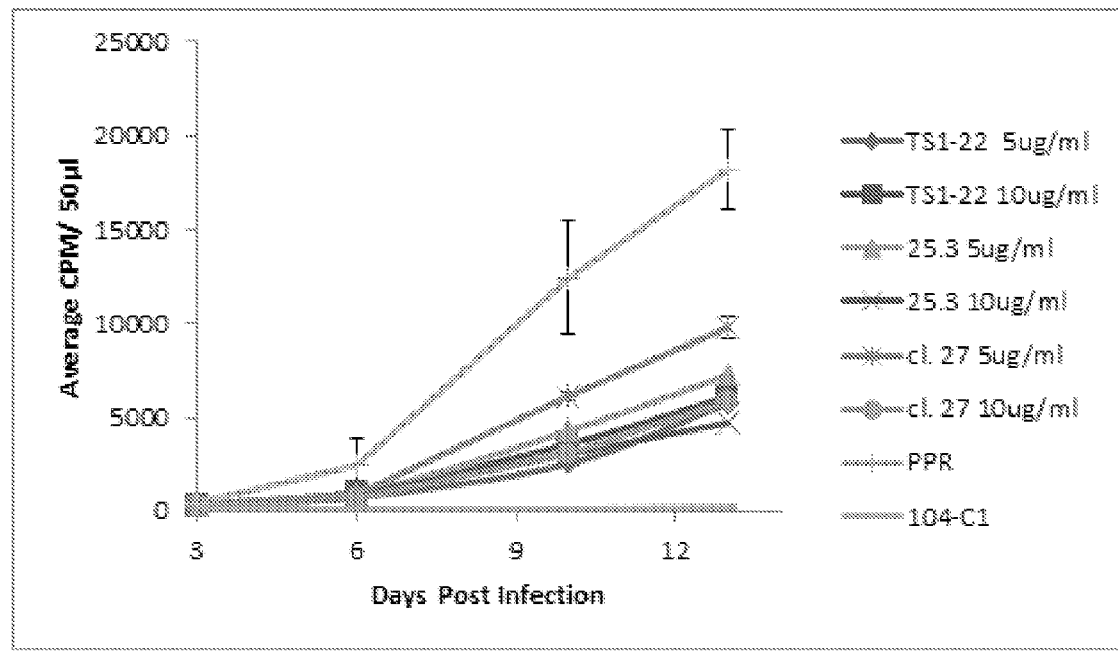
FIG. 2 is a graph showing the reverse transcriptase activity (counts per minute) in feline 104-C1 T-cells following a 2-hour spin inoculation with a preparation of FIV-PPR preincubated for 30 minutes with 0 µg/mL (control; PPR), 5 µg/mL, or 10 µg/mL TS1/22 antibody, clone 25.3 antibody, or clone 27 antibody, recovery for 3 hours at 37° C. and 5% $CO_2$, and an incubation in fresh media containing the identical concentrations of each antibody.

An exemplary anti-CD11a antibody or antigen-binding fragments thereof that can be used in any of the methods described herein is the antibody produced from clone 25.3 (Becker Coulter (PN IM0157 and PN IM1433U) and anti-gen-binding fragments of the antibody produced from clone 25.3, the antibody produced from clone 27 (BD Transduction Laboratories, No. 610826) and antigen-binding fragments of the antibody produced from clone 27, and TS1/22 and antigen-binding (feline CD11a-binding) fragments of TS1/22. The antibody produced from clone 25.3 has been described as having the ability to bind to an epitope on feline CD11a (Saalmüller et al., *Cell. Immunol.* 236:51-58, 2005). The antibody produced from clone 25.3 and the TS1/22 antibody have been shown to bind to the same epitope (IdeA) within the I domain of CD11a (Champe et al., *J. Biol. Chem.* 270:1388-1394, 1995), thus both the antibody produced by clone 25.3 and the TS1/22 antibody (and antigen-binding fragments of each antibody) can be used to perform the present methods. The data provided herein indicate that the antibody produced by clone 27 binds to CD11a, and prevents HIV infection of feline cells (FIG. 2).

Additional anti-CD11a antibodies are known in the art and include, for example antibodies produced from clone 2D7, HI111, M17/4, TS2/4, WT.1, or H155-78 (BioLegend, San Diego, Calif.), efalizumab, the antibody produced from clone MEM-25 (Antibodies Online, Aachen, Germany), and the anti-feline CD11a antibody described in Shimojima et al. (*Microbes and Infection* 5:1171-1176, 2003), or antigen-binding fragments thereof. Additional anti-CD11a antibodies can contain at least one CDR (e.g., of at least three light chain CDRs and/or at least three heavy chain CDRs) of the antibody produced from clone 25.3 (Becker Coulter (PN IM0157 and PN IM1433U), the antibody produced from clone 27 (BD Transduction Laboratories, No. 610826), or the anti-feline CD11a antibody described in Shimojima et al. (*Microbes and Infection* 5:1171-1176, 2003).

Additional antibodies or antigen-binding fragments useful in any of the methods described herein bind competitively with the antibody TS1/22 to feline CD11a (e.g., binds competitively with the antibody TS1/22 to a cell that expresses feline CD11a). Additional antibodies or antigen-binding fragments useful in any of the methods described herein bind competitively with the clone 25.3 antibody to feline CD11a (e.g., binds competitively with the clone 25.3 antibody to a cell that expresses feline CD11a) or bind competitively with the clone 27 antibody to feline CD11a (e.g., binds competitively with the clone 27 antibody to a cell that expresses feline CD11a). Additional anti-CD11a antibodies are known in the art.

Non-limiting examples of anti-CD18 antibodies or antigen-binding fragments thereof that can be used in any of the methods described herein include antibodies produced from clone M18/2, TS1/18, or WT.3 (BioLegend, San Diego, Calif.), the antibodies described in U.S. Patent Application Publication No. 2004/0101527, and the antibodies described in U.S. Pat. Nos. 6,689,869 and 5,914,112, or antigen-binding fragments thereof. Additional anti-CD18 antibodies are known in the art.

Non-limiting examples of anti-ICAM-1 antibodies or antigen-binding fragments thereof that can be used in any of the methods described herein include antibody #4915 (Cell Signaling Technology), sc-107 (Santa Cruz Biotechnology), RabMab® (Epitomics), anti-CD54 (Cell Applications, Inc.), the antibodies described in U.S. Patent Application Publication No. 2011/0052601, and the antibodies described in U.S. Pat. Nos. 5,324,510, 5,695,760, or antigen-binding fragments thereof. Additional anti-ICAM-1 antibodies are known in the art.

Small Molecules

Agents useful in the methods described herein also include small molecules. Small molecules useful in the methods described herein can be small organic (e.g., peptides, nucleotides, sugars, and/or lipids) or small inorganic molecules (e.g., metal complexes). Small molecules useful in the described methods may be identified using any of the screening methods described herein. Small molecules can block or decrease binding of LFA-1 to ICAM-1 by binding directly to CD11a, CD18, ICAM-1, or both CD11a and CD18. In some embodiments, the small molecule can bind LFA-1 at or around the same site that ICAM-1 binds to LFA-1. In some embodiments, the small molecule can bind LFA-1 at a site that is remote from the site that ICAM-1 binds to LFA-1 (e.g., the binding of the small molecule induces a change in the tertiary structure of LFA-1 that prevents or decreases binding of LFA-1 to ICAM-1, or the binding of the small molecule prevents the oligomerization or heterodimerization of LFA-1 that prevents or decreases the binding of LFA-1 to ICAM-1).

In some embodiments, the small molecule can bind ICAM-1 at or around the same site that LFA-1 binds to ICAM-1. In some embodiments, the small molecule can bind ICAM-1 at a site that is remote from the site that LFA-1 binds to ICAM-1 (e.g., the binding of the small molecule induces a change in the tertiary structure of ICAM-1 that prevents or decreases binding of ICAM-1 to a LFA-1, or the binding of the small molecule prevents the oligomerization of ICAM-1 that prevents or decreases the binding of ICAM-1 to LFA-1).

In some embodiments, the small molecules can block or decrease binding of LFA-1 to ICAM-1 by binding to another molecule (e.g., protein, lipid, and/or carbohydrate) that binds to CD11a, CD18, ICAM-1, or both CD11a and CD18.

Non-limiting examples of small molecules that can be used in any of the methods described herein include statin or statin derivatives. Lovastatin and simvastin have been demonstrated to inhibit LFA-1 activation (Wang et al., *Biol. Blood Marrow Transplant.* 15:1513-1522, 2009; Almog, *Chest* 124:740-743, 2003). Some statin derivatives (e.g., LFA878, LFA703, LFA451, and XVA143) have been identified as preventing the ability of CD11a to bind to ICAM-1 (Weitz-Schmidt et al., *J. Biol. Chem.* 279:46764-46771, 2004; Welzenbach et al., *J. Biol. Chem.* 277:10590-10598, 2002).

Thus, lovastatin, simvastin, lovastatin derivatives, simvastatin derivatives, LFA878, LFA703, LFA451, and XVA143, as well as other statins may prevent or decrease the ability of LFA-1 (comprising CD11a and CD18) from binding to ICAM-1.

Non-limiting examples of small molecules that can be used in any of the methods described herein include: lovastatin, simvastin, pravastatin, atorvastatin, fluvastatin, rosuvastatin, amplodipine, cerivastatin, mevastatin, pitavastatin, lovastatin derivatives, simvastatin derivatives, LFA878, LFA703, LFA451, and XVA143. In some embodiments of any of the methods described herein the small molecule is lovastatin, simvastin, a lovastatin derivative, a simvastatin derivative, LFA878, LFA703, LFA451, and XVA143, or a salt, solvate, or hydrate thereof.

Lovastatin has the following chemical structure:

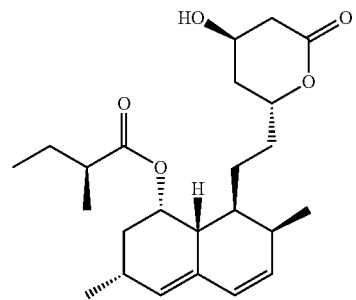 [SMILES: CC[C@H](C)C(=O)O[C@H]1C[C@@H](C)C=C2C=C[C@H](C)[C@H](CC[C@@H]3C[C@@H](O)CC(=O)O3)[C@H]21]

Derivatives of lovastatin can be generated using methods of chemical modification known in the art. For example, methods of generating derivatives of lovastatin, as well as lovastatin derivatives (e.g., exomethylene-modified, an 8-acyl-modified, or an alkylated lovastatin derivatives) are described in U.S. Pat. Nos. 4,866,186 and 6,472,542).

Simvastatin has the following chemical structure:

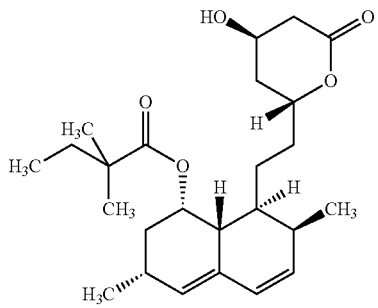 [SMILES: CCC(C)(C)C(=O)O[C@H]1C[C@@H](C)C=C2C=C[C@H](C)[C@H](CC[C@@H]3C[C@@H](O)CC(=O)O3)[C@H]21]

Derivatives of simvastatin can be generated using methods of chemical modification known in the art. For example, methods of generating derivatives of simvastatin, as well as simvastatin derivatives (e.g., 3-keto, 5-hydroxy-derivatives, di- and hydroxy derivatives) are described in U.S. Pat. Nos. 6,252,091; 6,541,511; 6,384,238; 6,252,091; 6,100,407; 5,393,893; 5,159,104; and 4,965,200; and in U.S. Patent Application Publication Nos. 2003/0176501 and 2002/0035274.

Additional methods for the modification of statins (e.g., lovastatin and simvastatin) are described in U.S. Pat. Nos. 5,134,124; 7,855,302; 5,462,716; 7,563,909; 7,420,078; 7,304,091; 7,297,808; and 7,166,638; and U.S. Patent Application Publication Nos. 2011/0054193; 2009/0118317; 2008/0289056; 2008/0096908; 2008/0090857; 2007/0072942; 2005/0228042; 2005/0165084; 2005/0148654; 2004/0235935; and 2004/0186313.

Statin derivatives (e.g., lovastatin and simvastatin derivatives) can be used in any of the methods described herein. The ability of a statin derivative, a simvastatin derivative, or a lovastatin derivate to decrease LFA-1 binding to ICAM-1 can be determined using affinity assays known in the art (e.g., BioCore technology) and assays described herein.

Additional small molecules that are useful in any of the methods described have the structure of Formula I:

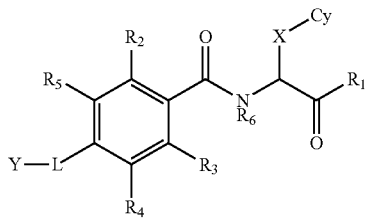

In Formula I, Cy is a non-aromatic carbocycle or heterocycle, optionally substituted with hydroxyl (—OH), mercapto (—SH), thioalkyl, a halogen (e.g., F, Cl, Br, or I), oxo (═O), thio (═S), amino, aminoalkyl, amidine (—C(NH)—NH$_2$), guanidine (—NH$_2$—C(NH)—NH$_2$), nitro, alkyl, or alkoxy. In some embodiments, Cy is a 3-5 member ring. In some embodiments, Cy is a 5- or 6-member non-aromatic heterocycle, optionally substituted with hydroxyl, mercapto, halogen (e.g., F or Cl), oxo (═O), thio (═S), amino, amidine, guanidine, nitro, alkyl, or alkoxy. In some embodiments, Cy is a 5-member non-aromatic heterocycle, optionally substituted with hydroxyl, oxo, thio, Cl, C$_{1-4}$ alkyl (e.g., methyl), or C$_{1-4}$ alkanoyl (e.g., acetyl, propanoyl, or butanoyl). In some embodiments, the non-aromatic heterocycle contains one or heteroatoms (N, O, or S) and is optionally substituted with hydroxyl, oxo, mercapto, thio, methyl, acetyl, propanoyl, or butyl. In some embodiments, the non-aromatic heterocycle contains at least one nitrogen atom that is optionally substituted with methyl or acetyl. In some embodiments, the non-aromatic heterocycle is selected from: piperidine, piperazine, morpholine, tetrahydrofuran, tetrahydrothiophene, oxazolidine, and thiazolidine, optionally substituted with hydroxy, oxo, mercapto, thio, alkyl, or alkanoyl. In some embodiments, Cy is a non-aromatic heterocycle selected from: tetrahydrofuran-2-yl, thiazolidin-5-yl, thiazolidin-2-one-5-yl, thiazolidin-2-thione-5-yl, and cyclopropapyrrolidine.

In some embodiments Cy is a 3-6 member carbocycle, optionally substituted with hydroxyl, mercapto, halogen, oxo, thio, amino, amidine, guanidine, alkyl, alkoxy, or acyl. In some embodiments, the carbocycle is saturated or partially unsaturated. In some embodiments Cy is a carbocycle selected from the group consisting of cyclopropyl, cyclopropenyl, cyclobutyl, cyclobutenyl, cyclopentyl, cyclopentenyl, cyclohexyl, and cyclohexenyl.

In Formula I, X is a C$_{1-5}$ divalent hydrocarbon linker, optionally having one or more carbon atoms replaced with N, O, S, SO, or SO$_2$, and is optionally substituted with hydroxyl, mercapto, halogen, amino, aminoalkyl, nitro, oxo, or thio. In some embodiments X will have at least one carbon atom. Replacements and substitutions can form an amide moiety (—NRC(O)— or —C(O)NR—) within the hydrocarbon chain or at either or both ends. Other moieties can include sulfonamide (—NRSO$_2$— or —SO$_2$NR), acyl, ether, thioether, and amine. In some embodiments, X is the group —CH$_2$—NR$_6$—C(O)—, where the carbonyl —C(O)— portion thereof is adjacent (i.e., covalently bonded) to Cy and R$_6$ is alkyl (e.g., methyl) or H.

In Formula I, Y is a carbocycle or heterocycle, optionally substituted with hydroxyl, mercapto, halogen, oxo, thio, a hydrocarbon, a halo-substituted hydrocarbon, amino, amidine, guanidine, cyano, nitro, alkoxy, or acyl. In some embodiments, Y is aryl or heteroaryl, optionally substituted with halogen or hydroxyl. In some embodiments, Y is phenyl, furan-2-yl, thiophene-2-yl, phenyl substituted with a halogen (e.g., Cl) or hydroxyl (e.g., at the meta position).

In Formula I, L is a divalent hydrocarbon, optionally having one or more carbon atoms replaced with N, O, S, SO, or SO$_2$, and optionally being substituted with hydroxyl, halogen, oxo, or thio; or three carbon atoms of the hydrocarbon are replaced with an amino acid residue. In some embodiments, L is less than 10 atoms or less than 5 atoms in length. In some embodiments, L is 5 or 3 atoms in length. In some embodiments, L is selected from: —CH═CH—C(O)—NR$_6$—CH$_2$—, —CH$_2$—NR$_6$—C(O)—, —C(O)—NR$_6$—CH$_2$—, —CH(OH)—(CH$_2$)$_2$—, —(CH$_2$)$_2$—CH(OH)—, —(CH$_2$)$_3$—, —C(O)—NR$_6$—CH(R$_7$)—C(O)—NR$_6$—, —NR$_6$—C(O)—CH(R$_7$)—NR$_6$—C(O)—, —CH(OH)—CH$_2$—O—, and —CH(OH)—CF$_2$—CH$_2$—, where each R$_6$ is independently H or alkyl, and R$_7$ is an amino acid side chain. Amino acid side chains can include non-naturally occurring side chains, such as phenyl, or naturally-occurring side chains. In some embodiments the side chains are Phe, Tyr, Ala, Gln, and Asn. In some embodiments, L is —CH═CH—C(O)—NR$_6$—CH$_2$—, where the —CH═CH— moiety is adjacent (i.e., covalently bounded) to Y. In some embodiments, L is —CH$_2$—NR$_6$—C(O)—, where the methylene moiety (—CH$_2$—) is adjacent to Y.

In Formula I, R$_1$ is H, OH, amino, O-carbocycle, or alkoxy, optionally substituted with amino, a carbocycle, or a heterocycle. In some embodiments, R$_1$ is H, phenyl, or $C_{1-4}$ alkoxy, optionally substituted with a carbocycle, such as phenyl. In some embodiments, $R_1$ is H. In some embodiments, $R_1$ is methoxy, ethoxy, propyloxy, butyloxy, isobutyloxy, s-butyloxy, t-butyloxy, phenoxy, or benzyloxy. In some embodiments $R_1$ is $NH_2$. In some embodiments, $R_1$ is ethoxy. In some embodiments, $R_1$ is isobutyloxy. In some embodiments, $R_1$ is an alkoxy substituted with amino, for example, 2-aminoethoxy, N-morpholinoethoxy, N,N-dialkyaminoethoxy, or quaternary ammonium hydroxy alkoxy (e.g., trimethylammoniumhydroxyethoxy).

In Formula I, $R_{2-5}$ are independently H, hydroxyl, mercapto, halogen, cyano, amino, amidine, guanidine, nitro, or alkoxy; or $R_3$ and $R_4$ together form a fused carbocycle or heterocycle, optionally substituted with hydroxyl, halogen, oxo, thio, amino, amidine, guanidine, or alkoxy. In some embodiments, $R_2$ and $R_3$ are independently H, F, Cl, Br, or I. In some embodiments, $R_4$ and $R_5$ are both H. In some embodiments, one of $R_2$ and $R_3$ is a halogen, while the other is hydrogen or a halogen. In some embodiments, $R_3$ is Cl, while $R_2$, $R_4$, and $R_5$ are each H. In some embodiments, $R_2$ and $R_3$ are both Cl, while $R_4$ and $R_5$ are both H.

$R_6$ is H or a hydrocarbon chain, optionally substituted with a carbocycle or a heterocycle. In some embodiments, $R_6$ is H or alkyl (e.g., methyl, ethyl, propyl, butyl, i-butyl, s-butyl, or t-butyl). In some embodiments $R_6$ is H. Non-limiting specific examples of compounds of Formula I are shown in FIGS. 1A-F. Additional examples of small molecules of Formula I are described in U.S. Pat. No. 6,872,735 (herein incorporated by reference in its entirety).

Small molecules of Formula I can be prepared according to established organic synthesis techniques from starting materials and reagents that are commercially available. Many standard chemical techniques and procedures are described in March, J., "Advanced Organic Chemistry," McGraw-Hill, New York, 1977; and Collman, J., "Principles and Applications of Organotransition Metal Chemistry," University Science, Mill Valley, 1987; and Larock, R., "Comprehensive Organic Transformations," Verlag, New York, 1989. Depending on the particular substituents present on the compounds, suitable protection and deprotection procedures may be required. Numerous protecting groups are described in Greene and Wuts, "Protective Groups in Organic Chemistry," 2nd Edition, John Wiley and Sons, 1991, as well as detailed protection and deprotection procedures. For example, suitable amino protecting groups include t-butyloxycarbonyl (Boc), fluorenylmethyloxycarbonyl (Fmoc), 2-trimethylsilylethyoxycarbonyl (Teoc), 1-methyl-1-(4-biphenylyl)ethoxycarbonyl (Bpoc), allyloxycarbonyl (Alloc), and benzyloxycarbonyl (Cbz). Carboxyl groups can be protected as fluorenylmethyl groups or alkyl esters (e.g., methyl, ethyl, or alkenyl esters, such as allyl). Hydroxyl groups can be protected with trityl, monomethoxytrityl, dimethoxytrityl, and trimethoxytrityl groups. Additional specific methods for generating small molecules of Formula I are described in U.S. Pat. No. 6,872,735 (herein incorporated by reference in its entirety).

Veterinary Compositions

Also provided herein are veterinary compositions that contain at least one (e.g., one, two, three, four, or five) of the agents described herein. In some embodiments, the at least one agent decreases (e.g., significantly decreases) or inhibits binding of a LFA-1 to ICAM-1 in a feline.

Two or more (e.g., two, three, four, or five) agents can be present in a veterinary composition in any combination, e.g., two or more proteins (e.g., antibodies and/or antigen-binding antibody fragments), two or more small molecules (e.g., lovastatin, simvastatin, lovastatin derivatives, simvastatin derivatives, LFA703, LFA451, LFA878, XVA143, or any compound of Formula I, or any combination thereof), or combinations of at least one protein (e.g., antibodies and/or antigen-binding antibody fragments) and at least one small molecule (e.g., lovastatin, simvastatin, lovastatin derivatives, simvastatin derivatives, LFA703, LFA451, LFA878, XVA143, or any compound of Formula I, or any combination thereof).

The veterinary compositions may be formulated in any manner known in the art. Veterinary compositions are formulated to be compatible with their intended route of administration, whether oral or parenteral (e.g., intravenous, intradermal, subcutaneous, intraperitoneal, transmucosal, or transdermal (e.g., topical ointments, salves, gels, patches or creams as generally known in the art)). The compositions can include a sterile diluent (e.g., sterile water or saline), a fixed oil, polyethylene glycol, glycerine, propylene glycol or other synthetic solvents; antibacterial or antifungal agents such as benzyl alcohol or methyl parabens, chlorobutanol, phenol, ascorbic acid, thimerosal, and the like; antioxidants such as ascorbic acid or sodium bisulfite; chelating agents such as ethylenediaminetetraacetic acid; buffers such as acetates, citrates or phosphates; and isotonic agents such as sugars (e.g., dextrose), polyalcohols (e.g., manitol or sorbitol), or salts (e.g., sodium chloride). Liposomal suspensions (including liposomes targeted to affected cells with monoclonal antibodies specific for the target feline cell) can also be used as pharmaceutically acceptable carriers (see, e.g., U.S. Pat. No. 4,522,811). Preparations of the compositions can be formulated and enclosed in ampules, disposable syringes, or multiple dose vials. Where required (as in, for example, injectable formulations), proper fluidity can be maintained by, for example, the use of a coating such as lecithin, or a surfactant. Absorption of the active ingredient can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

Where oral administration is intended, the agent can be included in pills, capsules, troches, and the like, and can contain any of the following ingredients, or compounds of a similar nature: a binder, such as microcrystalline cellulose, gum tragacanth or gelatin; an excipient, such as starch or lactose, a disintegrating agent, such as alginic acid, Primogel, or corn starch; a lubricant, such as magnesium stearate; a glidant, such as colloidal silicon dioxide; a sweetening agent, such as sucrose or saccharin; or a flavoring agent, such as methyl salicylate or fish flavoring.

Compositions containing one or more of any of the agents described herein can be formulated for oral or parenteral administration in dosage unit form (i.e., physically discrete units containing a predetermined quantity of active compound for ease of administration and uniformity of dosage). In some embodiments, one or more agents can be administered to the feline as a component of a food composition (e.g., a pellet, powder, or semi-sold slurry) or liquid (e.g., a syrup) for oral ingestion.

Toxicity and therapeutic efficacy of compositions can be determined by standard pharmaceutical procedures in cell cultures or experimental animals (e.g., felines). One can, for example, determine the LD50 (the dose lethal to 50% of the population) and the ED50 (the dose therapeutically effective in 50% of the population), the therapeutic index being the ratio of LD50:ED50. Agents that exhibit high therapeutic indices are preferred. Where an agent exhibits an undesirable side effect, care should be taken to target that agent to the site of the affected tissue (the aim being to minimize potential damage to unaffected cells and, thereby, reduce side effects). Toxicity and therapeutic efficacy can be determined by other standard pharmaceutical procedures.

Data obtained from cell culture assays and animal studies can be used in formulating an appropriate dosage of any given agent for use in felines. A therapeutically effective amount of the one or more agent will be an amount that treats or decreases the risk of developing a retroviral infection in a feline, decreases the severity, frequency, and/or duration of one or more symptoms of a retroviral infection in a feline, increases the ratio of CD4$^+$ T-cells to CD8$^+$ T-cells in a feline with a retroviral infection, increases the number of CD4$^+$ T cells in a feline with a retroviral infection, and/or increases the total white blood cell count in a feline with a retroviral infection (e.g., as compared to a control feline having a retroviral infection or the same feline prior to treatment). The effectiveness and dosing of any of the agents described herein can be determined by a veterinary professional using methods known in the art, as well as by the observation of one or more symptoms of retroviral infection in a feline. Certain factors may influence the dosage and timing required to effectively treat a feline (e.g., the severity of the infection or disease, previous treatments, the general health and/or age of the feline, and the presence of other diseases).

As noted herein, agents administered according to the methods described herein can be small molecules (e.g., peptides, peptidomimetics (e.g., peptoids), amino acid residues (or analogs thereof), polynucleotides (or analogs thereof), nucleotides (or analogs thereof), or organic or inorganic compounds (e.g., heteroorganic or organometallic compounds)). Typically, such molecules will have a molecular weight less than about 10,000 grams per mole (e.g., less than about 7,500, 5,000, 2,500, 1,000, or 500 grams per mole). Salts, esters, and other pharmaceutically acceptable forms of any of these compounds can be assayed and, if a desirable activity is detected, administered according to the therapeutic methods described herein. The agents administered according to the methods described herein can be proteins (e.g., antibodies or antigen-binding fragments thereof).

Exemplary doses include milligram or microgram amounts of any of the agents described herein per kilogram of the feline's weight (e.g., about 1 μg-500 mg/kg; about 100 μg-500 mg/kg; about 100 μg-50 mg/kg; 10 μg-5 mg/kg; 10 μg-0.5 mg/kg; or 1 μg-50 μg/kg). While these doses cover a broad range, one of ordinary skill in the art will understand that therapeutic agents, including small molecules, vary in their potency, and effective amounts can be determined by methods known in the art. Typically, relatively low doses are administered at first, and the attending veterinary professional (in the case of therapeutic application) or a researcher (when still working at the development stage) can subsequently and gradually increase the dose until an appropriate response is obtained. In addition, it is understood that the specific dose level for any particular feline will depend upon a variety of factors including the activity of the specific compound employed, the age, body weight, general health, gender, and diet of the feline, the time of administration, the route of administration, the rate of excretion, any drug combination, and the degree of activity to be modulated.

The veterinary compositions can be included in a container, pack, or dispenser together with instructions for administration.

Methods of Treating Retroviral Infection in a Feline

Provided herein are methods for treating or reducing the likelihood of developing a retroviral infection in a feline. Also provided are methods for reducing retroviral virion entry (e.g., fusion) into a feline target cell (e.g., a non-infected cell), retroviral virion budding from a feline cell, and syncytium transmission in a feline. All of the methods described herein require administering to the feline at least one agent that prevents or reduces the binding of LFA-1 (e.g., present in or on the surface of a non-infected feline cell, a virion, or a syncytium) from binding to ICAM-1 (e.g., present in a non-infected feline cell, a virion, or a syncytium). In some embodiments, the at least one agent specifically binds to CD11a, CD18, ICAM-1, or an epitope formed by both CD11a and CD18 (e.g., present in or on the surface of a non-infected target cell and/or present in or on the surface of a virion and/or syncytium). In some embodiments, the at least one agent binds directly to CD11a, CD18, ICAM-1, or an epitope formed by both CD and CD18. In some embodiments, the at least one agent indirectly binds to CD11a, CD18, ICAM-1, or an epitope formed by both CD11a and CD18. In any of the methods described herein, the at least one agent can be formulated or administered as one or more of the veterinary compositions described herein.

In some embodiments, the feline is a domestic feline. In some embodiments, the feline that is treated can be previously diagnosed as having a retroviral infection (e.g., FIV or FELV). A feline can be diagnosed as having a retroviral infection by a veterinary professional using any of the methods described herein (e.g., by the observation of at least one symptom of a retroviral infection in a feline) or any methods known in the art. In some embodiments, the feline that is treated can be identified as having an increased risk of developing a retroviral infection (e.g., FIV and FELV). For example, a feline can be determined to have an increased risk of retroviral infection in view of a local pandemic of retroviral infection or by its proximity to one or more other felines having or suspected of having a retroviral infection. A determination or prediction of the incidence of retroviral infection in a population of felines can be assessed or determined by public health officials. In any of the methods described herein, the feline may be treated by its owner (e.g., a domestic feline), a veterinary professional, or a public health worker.

In some embodiments, the agent is an antibody or an antigen-binding fragment thereof that binds specifically to CD11a, CD18, ICAM-1, or an epitope formed by both CD11a and CD18. In some embodiments, the antibody or an antigen-binding fragment thereof prevents or reduces LFA-1 from binding to ICAM-1. Any of the antibodies or antibodies fragments described herein can be used alone or in any combination in any of the methods described herein. In a non-limiting example, the at least one agent used in any of the methods described herein can be a monoclonal antibody, a chimeric antibody, a single-chain antibody (e.g., a single-domain antibody), a feline antibody, or a felinized antibody.

In some embodiments of any of the methods described herein, the at least one agent can be any of the small molecules described herein. In a non-limiting example, the small molecule can be a statin or a statin derivative (e.g., any of the statins or statin derivatives described herein, such as lovastatin, simvaststin, a lovastatin derivative (6-exomethylene-modified, an 8-acyl-modified, or an alkylated lovastatin), and/or a simvastatin derivative). Additional small molecules that can be used in any of the methods described herein include LFA703, LFA451, LFA878, and XVA143. Additional small molecules that can be used in any of the methods described herein include molecules of Formula I (as described herein). Non-limiting examples of small molecules of Formula I that can be used in any of the methods described herein are shown in FIGS. 1A-F. Additional examples of small molecules of Formula I that can be used in any of the methods described herein are listed in U.S. Pat. No. 6,872,735 (herein incorporated by reference in its entirety).

In some embodiments of any of the methods described herein, the methods include administering to a feline at least one small molecule that prevents or decreases LFA-1 binding to ICAM-1 and/or at least one antibody or antigen-binding fragment thereof that specifically binds to CD11a, CD18, ICAM-1, or an epitope formed by both CD11a and CD18, where the at least one small molecule or the at least one antibody or antigen-binding fragment thereof is administered in an amount sufficient to treat a retrovirus infection, reduce the entry (e.g., fusion) of a retroviral virion into a feline cell, reduce the budding of retroviral virions from a feline cell, and/or reduce syncytium transmission in a feline. The effect of a small molecule and/or an antibody or antigen-binding fragment thereof (as described herein) on virion fusion and/or budding from a feline cell, as well as syncytium transmission can be studied in vitro (in tissue culture) using, for example, microscopic techniques. The data from these in vitro studies can be used to predict the effect of the small molecule and/or antibody or antigen-binding fragment thereof (as described herein) on syncytium transmission in a feline. A decrease in syncytium transmission can also result in a decrease in or a delay in the onset of dementia in a feline having a retroviral (FIV) infection. Feline dementia can be diagnosed by a veterinary care professional or by a feline's owner (for a domestic feline) by the observation of specific behaviors by the feline (e.g., the feline seems to get lost or confused in familiar surroundings, inability or difficulty in finding a litter box (for a domestic feline), or a decrease in the response to an owner's vocal greeting or command).

In some embodiments, the feline is administered at least one antibody or antigen-binding fragment thereof that specifically binds to CD11a, CD18, ICAM-1, or an epitope formed by both CD11a and CD18 (e.g., present in or on the surface of a non-infected feline cell or present in or on the surface of a virion or syncytium). In some embodiments of any of the methods described herein, the feline is administered at least one antibody or antigen-binding fragment thereof that prevents LFA-1 from binding to ICAM-1.

In some embodiments, the feline can be administered at least one antibody or antigen-binding fragment thereof that contains at least one complementary determining region (CDR) from the light chain or the heavy chain of TS1/22 antibody. In some embodiments, the feline can be administered at least one antibody or antigen-binding fragment thereof that contains the three CDRs from the light chain of TS1/22 antibody or the three CDRs from the heavy chain of TS1/22 antibody. In some embodiments, the feline can be administered an antibody or an antigen-binding fragment thereof that contains the three CDRs from the light chain of TS1/22 antibody and the three CDRs from the heavy chain of TS1/22 antibody.

In some embodiments of any of the methods described herein, the at least one antibody can be a feline antibody or an antigen-binding fragment thereof, or a felinized antibody or an antigen-binding fragment thereof. In some embodiments of any of the methods described herein, the antibody can be a single-chain antibody (e.g., a single-domain antibody). In some embodiments of any of the methods described herein, the at least one antigen-binding fragment thereof can be a Fab fragment, a F(ab')2 fragment, or a scFv fragment.

In some embodiments of any of the methods described herein, the feline is administered at least one (e.g., at least 1, 2, 3, 4, 5, 6, 7, 8, 9, 10, 15, 20, 25, or 30) dose of a composition containing at least one of any of the agents described herein (e.g., administered at least one dose of any of the veterinary compositions described herein). In any of the methods described herein, at least one agent (e.g., any of the agents described herein) or at least one veterinary composition (e.g., any of the veterinary compositions described herein) can be administered intravenously, intaarterially, ocularly, orally, subcutaneously, intraperitoneally, or intramuscularly to the feline. In some embodiments, the at least one agent (e.g., small molecule) or at least one veterinary composition containing a small molecule is administered orally. In some embodiments, at least one antibody or antigen-binding fragment thereof or at least one veterinary composition containing an antibody or antigen-binding fragment thereof is administered intravenously. In some embodiments of any of the methods described herein, a feline is administered at least one agent that is a small molecule (e.g., a small molecule that prevents or reduces LFA-1 from binding to ICAM-1, e.g., any of the small molecules described herein) or at least one veterinary composition that contains a small molecule, and at least one antibody or antigen-binding fragment thereof (e.g., an antibody or antigen-binding fragment thereof that specifically binds to CD11a, CD18, ICAM-1, or an epitope formed by both CD11a and CD18) or at least one veterinary composition that contains an antibody or antigen-binding fragment thereof (e.g., an antibody or antigen-binding fragment thereof that specifically binds to CD11a, CD18, ICAM-1, or an epitope formed by both CD11a and CD18). In some embodiments, at least one small molecule agent and at least one antibody or antigen-binding fragment thereof are administered in the same composition (e.g., the same veterinary composition). In some embodiments, at least one small molecule and at least one antibody or antigen-binding fragment thereof are administered to the feline using different routes of administration.

In some embodiments, the administering of at least one of any of the agents or at least one of any of the veterinary compositions described herein results in a decrease in the severity, frequency, or duration of at least one symptom of a retroviral infection in the feline. In some embodiments, the administering of at least one of any of the agents or at least one of any of the veterinary compositions described herein results in a decrease in retroviral titer in the feline. In some embodiments, the administering of at least one agent or at least one veterinary composition as described herein results in an increase (e.g., a significant increase in the ratio of $CD4^+$ T-cells to $CD8^+$ T-cells in the feline (e.g., a feline having FIV or SELV).

In any of the methods described herein, the at least one agent or the at least one veterinary composition can be administered to the feline at least once a week (e.g., twice a week, three times a week, four times a week, once a day, twice a day, or three times a day). In some embodiments, at least one small molecule and/or at least one antibody and/or antigen binding fragment thereof is administered to the feline at least once a week (e.g., twice a week, three times a week, four times a week, once a day, twice a day, or three times a day). In some embodiments, at least two different agents are administered in the same composition (e.g., a solid composition or liquid composition). In some embodiments, at least two different agents are administered in two different compositions (e.g., a solid composition and a liquid composition). In some embodiments, the at least one agent is administered as a component of a feed composition (e.g., pellets, a liquid, or a semi-solid slurry).

In some embodiments, the feline can be administered the at least one agent or at least one veterinary composition over an extended period of time (e.g., over a period of at least 1 week, 2 weeks, 3 weeks, 1 month, 2 months, 3 months, 4 months, 5 months, 6 months, 7 months, 8 months, 9 months, 10 months, 11 months, or 12 months). A skilled veterinary professional may determine the length of treatment period using any of the methods described herein for diagnosing or following the effectiveness of retroviral treatment (e.g., the observation of at least one symptom of a retroviral infection in a feline or retroviral titers in the feline). As described herein, a skilled veterinary professional can also change the identity and number (e.g., increase or decrease) of agents administered to the feline and can also adjust (e.g., increase or decrease) the dosage or frequency of administration of at least one agent to the feline based on assessment of the effectiveness of retroviral treatment (e.g., using any of the methods described herein and known in the art).

In some embodiments, the feline can be administered the at least one agent or the at least one veterinary composition during a time of feline retroviral outbreak (e.g., starting at any time before or during the retroviral outbreak and ending at a time when the incidence of infected felines in the population has significantly decreased).

In some embodiments, the administration of at least one agent or at least one veterinary composition described herein does not cause detrimental immunosuppression in the feline. Detrimental immunosuppression, for example, can be indicated by a nearly complete suppression of $CD8^+$ T-cell activation (cytotoxic T-lymphocyte activation) in a feline following therapeutic treatment.

In some embodiments, the retroviral infection treated is FIV or FELV. In some embodiments, the virion or syncytium is FIV or FELV.

In some embodiments of the methods described herein, the feline may be further administered one or more (e.g., one, two, three, or four) additional therapeutic agents (e.g., a sedative, an analgesic, or an anti-inflammatory agent). The one or more additional therapeutic agents and the at least one agent (e.g., any of the agents described herein) can be administered in the same dose. In some embodiments, the one or more additional therapeutic agents and the at least one agent (e.g., any of the agents described herein) can be administered in separate dosage forms. In some embodiments, the one or more additional therapeutics can be administered to the feline prior to administering at least one agent (e.g., any of the agents described herein). In some embodiments, the one or more additional therapeutics can be administered to the feline after administering at least one agent (e.g., any of the agents described herein). In some embodiments, the one or more additional therapeutics and the at least one agent are administered to the feline such that there is overlap in the bioactive period of the one or more additional therapeutics and the at least one agent in the feline.

Methods of Screening for Anti-Retroviral Agents

Also provided herein are methods of identifying candidate agents that can be useful for treating or decreasing the risk of retroviral infection in a feline, for decreasing virion entry (e.g., fusion) into a feline cell, for decreasing virion budding from a feline cell, or for decreasing syncytium transmission in a feline. These methods include providing LFA-1 and ICAM-1, and contacting the LFA-1 to ICAM-1 in the presence of the candidate agent, and determining the binding of LFA-1 to ICAM-1 in the presence of the candidate agent, where a decrease in the amount of binding between LFA-1 to ICAM-1 compared to the binding observed in the absence of the candidate agent indicates that the candidate agent can be useful for treating or decreasing the risk of retroviral infection in a feline, for decreasing virion entry into a feline cell, for decreasing virion budding from a feline cell, or for decreasing syncytium transmission in a feline.

In some embodiments of these methods, the LFA-1 may be expressed on the surface of a cell (e.g., a feline cell) and ICAM-1 is a recombinant soluble form of ICAM-1 protein. In some embodiments of these methods, the LFA-1 may be a recombinant form of soluble LFA-1 protein and ICAM-1 is expressed on the surface of a cell (e.g., a feline cell). In some embodiments, both LFA-1 and ICAM-1 are recombinant soluble proteins (e.g., and interactions identified by co-immunoprecipitation reactions).

In some embodiments of these methods, LFA-1 can be attached to a solid surface (e.g., a magnetic bead) and ICAM-1 is a recombinant soluble ICAM-1 protein. In some embodiments, ICAM-1 is attached to a solid surface (e.g., a magnetic bead) and LFA-1 is a recombinant soluble LFA-1 protein.

In some embodiments of any of the methods described herein, LFA-1 and/or ICAM-1 (including recombinant soluble forms of LFA-1 and/or ICAM-1) may be labeled (e.g., a fluorescent label, a radioisotope, or peptide-tag) for detection (e.g., detection by fluorescence, luminescence, or binding by a secondary antibody).

Candidate agents identified using any of the assays described herein can be further tested in a feline model of retroviral infection. The efficacy of the candidate agent to treat or reduce the number, severity, duration, or frequency of one or more symptoms of a retroviral infection in a feline can be determined using any of the methods described herein.

EXAMPLES

The invention is further described in the following examples, which do not limit the scope of the invention described in the claims.

Example 1

Antibodies that Specifically Bind to LFA-1 Decrease

An experiment was performed to determine whether an antibody that specifically binds to LFA-1 would decrease HIV infection in a FIV-susceptive, feline T-cell line (104-C1). In these experiments, FIV strain PPR ("PPR") was produced in 104-C1 cells. The resulting viral preparation was incubated with 0 µg/mL antibody (control), or 5 µg/mL or 10 µg/mL of anti-LFA1 antibody TS1/22 (produced from ATCC deposit number HB202), clone 25.3 (Becker Coulter (PN IM0157 and PN IM1433U), or clone 27 (BD Transduction Laboratories, No. 610826) for 30 minutes (at 37° C. and 5% $CO_2$) before being added to 150,000 104-C1 cells, and spin inoculated for 2 hours at 3,000 rpm. After spinning, the cells were recovered for 3 hours at 37° C. and 5% $CO_2$, before the viral media was replaced with fresh media containing the same concentrations of diluted antibody. After 6, 12, and 14 days of incubation in fresh medium, the cells were lysed and the reverse transcriptase activity in the cells was determined (counts per minute). The resulting data show that three different antibodies that specifically bind to LFA-1 significantly decrease HIV infection in feline T-cells (FIG. 2). These data indicate that antibodies or antigen-binding fragments thereof that specifically bind to LFA-1, or its binding partner ICAM-1, can decrease retrovirus infection (e.g., HIV infection) in a feline and can reduce retrovirus virion entry (e.g., FIV virion entry) into a feline cell. These data further indicate that small molecules that decrease binding of LFA-1 to its binding partner ICAM-1 can decrease retrovirus infection (e.g., HIV infection) in a feline and can reduce retrovirus virion entry (e.g., FIV virion entry) into a feline cell.

Example 2

Anti-CD11a Antibody and FIV Infection

Various additional experiments may be performed to determine whether an anti-CD11a antibody would decrease or prevent HIV infection in feline cells. For example, in such experiments, TS1/22 antibody (anti-CD11a antibody) may be incubated with either feline peripheral blood mononuclear cells or the feline T-cell line 104-C1 and binding assayed by fluorescence-assisted cell sorting (FACS).

In additional experiments, feline 104-C1 T-cells may be left untreated or pre-incubated for 15 minutes with TS1/22 (10 μg/mL or 50 μg/mL). The cells may then be washed and infected with FIV-PPR. The presence of virus may be determined by measuring reverse transcriptase activity at days 4, 7, 10, and 14. In one set of controls, the cells may be left untreated with TS1/22 and uninfected with FIV.

Example 3

Felinized Anti-CD11a Antibody

A. MHC306 Feline mAb Felinization Design

The felinization design of mouse antibody referred to herein as the MHC306 Feline mAb and corresponding to a felinized version of the anti-LFA1 antibody TS1/22 (produced from ATCC deposit number HB202) was performed using in silico analyses. The felinization process began by generating a homology modeled antibody 3D structure and creating a profile of the parental antibody based on structure modeling. Acceptor frameworks to utilize were identified based on the overall sequence identity across the framework, matching interface position, similarly classed CDR canonical positions, and presence of N-glycosylation sites that would have to be removed. Two light chain (LC) and two heavy chain (HC) frameworks were selected for the felinization design.

Felinized antibodies were designed by creating multiple hybrid sequences that fuse select parts of the parental antibody sequence with the feline framework sequences. Using the 3D model, these felinized sequences were methodically analyzed by eye and computer modeling to isolate the sequences that would most likely retain antigen binding. The goal was to maximize the amount of feline sequence in the final felinized antibodies while retaining the original antibody specificity.

Three felinized light chains and three felinized heavy chains were designed based on two different heavy and light chain feline acceptor frameworks (see table below). The first felinized chain for each utilizes the first respective framework and contains the most feline sequence with minimal parental antibody framework sequence (Felinized LC 1, HC 1). The second felinized chain for each uses the same framework as before but contains additional parental sequences (Felinized LC 2, HC 2). The third felinized chain for each utilizes the second respective framework and, similar to LC 2/HC 2, also contains additional parental sequences fused with the feline framework (Felinized LC 3, HC 3). Below is a table of the MHC306 Feline mAb felinized chains that were designed. The 7xxx numbers correspond to internal codes used to distinguish the DNA sequences of the respective antibody chains.

| Chain Name | Chain Type | Acceptor framework |
|---|---|---|
| 7302 (Felinized LC 1) | Light Chain | LC framework 1 |
| 7303 (Felinized LC 2) | Light Chain | LC framework 1 |
| 7304 (Felinized LC 3) | Light Chain | LC framework 2 |
| 7299 (Felinized HC 1) | Heavy Chain | HC framework 1 |
| 7300 (Felinized HC 2) | Heavy Chain | HC framework 1 |
| 7301 (Felinized HC 3) | Heavy Chain | HC framework 2 |

The light and heavy felinized chains were then combined to create variant fully felinized antibodies. Possible combinations of light and heavy chains were tested for their expression level and antigen binding affinity to identify antibodies that performed similar to the parental MHC306 Feline mAb antibody.

B. Construction of Felinized MHC306 Feline mAb Antibodies

Full-length antibody genes were constructed by first synthesizing the variable region sequences. The sequences were optimized for expression in Chinese hamster ovary (CHO) cells. These variable region sequences were then cloned into expression vectors that already contain feline Fc domains IgG1 for heavy chain, kappa for light chain). In addition, for comparison, the chimeric antibody using the same backbone Fc sequences was used as a control.

C. Cell Binding Analysis of Felinized MHC306 Feline mAb Antibodies

Including the parental antibody sequences, a 4×4 matrix of 16 antibody combinations were transiently expressed in CHO cells, and their expression levels were evaluated by ELISA. Affinity to the antigen was determined by performing a cell binding assay with feline MCH-4 cells expressing the LEA-1 antigen.

For cell binding assays, supernatants from transiently transfected CHO cells were added to MCH-4 cells for 1 hour at room temperature. After washing with PBS, HRP conjugated goat anti-feline IgG antibody was incubated for 1 hour at room temperature. The cells were washed and then the HRP substrate TMB was added to each well for color development. Raw data was collected by POLARstar Omega from BMG Labtech. For expression analysis, ELISA plates were blocked with 1% casein for 2 hours to reduce non-specific binding. Supernatants were diluted in 5-fold increments for a total of eight data points and were added to the ELISA wells for 1 hour at 37° C., The plates were washed with a wash buffer, and then incubated with HRP conjugated goat anti-feline IgG antibody for 1 hour. The plates were washed with a wash buffer, and then the HRP substrate TMB was added to each well for color development. Raw data was collected by POLARstar Omega from BMG Labtech.

The 16 antibodies tested are shown here, Number 1 is the parental MHC306 Feline mAb chimeric antibody, and the nine fully felinized antibodies are also shown. The parental and felinized heavy and light chains that were used for each antibody pair are indicated.

| Antibody numbering | 7262 (Parental HC) | 7299 (Felinized HC 1) | 7300 (Felinized HC 2) | 7301 (Felinized HC 3) |
|---|---|---|---|---|
| 7263 (Parental LC) | #1 | #5 | #9 | #13 |
| 7302 (Felinized LC 1) | #2 | #6 | #10 | #14 |
| 7303 (Felinized LC 2) | #3 | #7 | #11 | #15 |
| 7304 (Felinized LC 3) | #4 | #8 | #12 | #16 |

Figure 3:
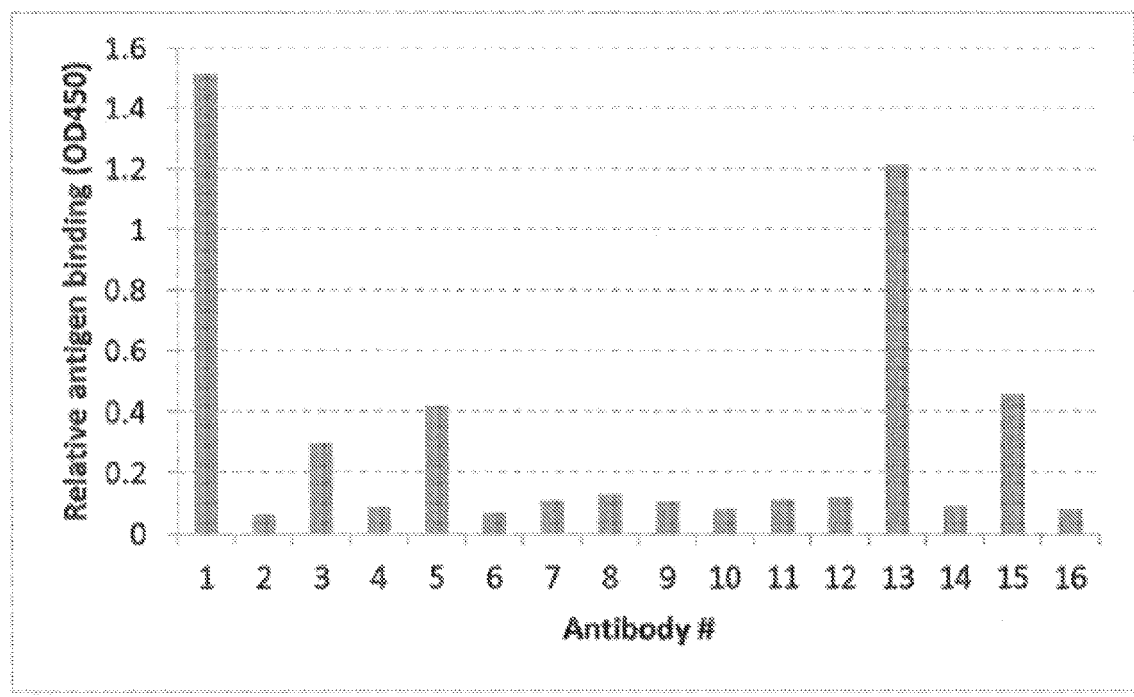
FIG. 3 is a graph showing the antigen binding data from MCH-4 cell binding assays.

The antigen binding data from the MCH-4 cell binding assays is depicted in FIG. 3.

D. Data Analysis of Felinized MHC306 Feline mAb Antibodies

The relative expression level of each antibody pair in CHO cells is shown below, as determined by ELISA. The values were calculated as ng/ml and then normalized relative to the level of expression of the parental antibody, where numbers near 1 have comparable expression levels to the parental antibody. Antigen binding affinity was determined by MCH-4 cell binding assay. In this initial screen, the values were normalized relative to the level of parental antibody antigen binding, where numbers near 1 have a comparable affinity to the antigen as the parental antibody. Additional expression and affinity data should be obtained by using purified antibodies and repeating the experiments.

| | 7262 (Parental HC) | 7299 (Felinized HC 1) | 7300 (Felinized HC 2) | 7301 (Felinized HC 3) |
|---|---|---|---|---|
| Relative expression level [higher = better expression] | | | | |
| 7263 (Parental LC) | 1.00 | 2.20 | 0.02 | 4.67 |
| 7302 (Felinized LC 1) | 5.57 | 3.09 | 0.10 | 2.33 |
| 7303 (Felinized LC 2) | 2.81 | 3.34 | 0.06 | 0.92 |
| 7304 (Felinized LC 3) | 0.06 | 0.00 | 0.00 | 0.00 |
| | | 7299 | 7300 | 7301 |
| Relative antigen binding [higher = better affinity] | | | | |
| 7263 (Parental LC) | 1.00 | 0.28 | 0.07 | 0.80 |
| 7302 (Felinized LC 1) | 0.04 | 0.05 | 0.05 | 0.06 |
| 7303 (Felinized LC 2) | 0.20 | 0.07 | 0.07 | 0.30 |
| 7304 (Felinized LC 3) | 0.06 | 0.09 | 0.08 | 0.05 |

E. Selection of the Felinized BC 3+Felinized LC 2 (#15) Antibody for 0.1 Liter Scale Production All antibodies containing Felinized HC 2 or LC 3 did not express. Accordingly, any antibodies containing either of these chains were not pursued.

The Felinized HC+Felinized LC 2 (#15) antibody, however, was scaled up to 0.1 liter scale and its expression and binding abilities as a purified antibody were tested as described below. It is noted that the Felinized HC 3+Felinized LC 2 (#15) is the only fully felinized antibody that showed binding to the antigen above background (about 3-fold less affinity than the chimeric).

F. 0.1 Liter Scale Production and Purification

Figure 4:
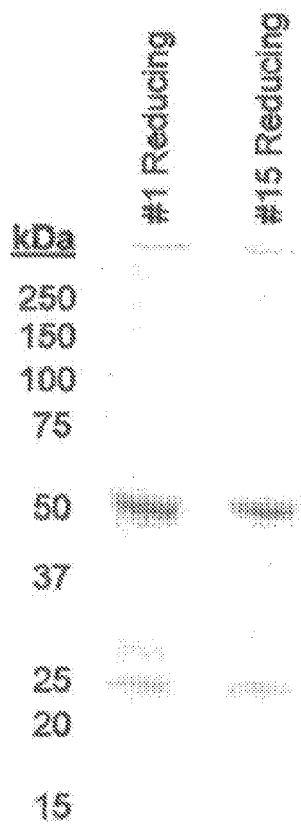
FIG. 4 shows SDS-PAGE images of the purified antibodies.

Felinized HC 3+Felinized LC 2 antibody #15 was selected for 0.1 liter scale production. The parental antibody was also scaled-up for direct comparison. Plasmids for the indicated heavy and light chains were transfected into suspension CHO cells using chemically defined media in the absence of serum to make the antibodies. Seven days after transfection, the conditioned media was collected and clarified. Whole antibodies in the conditioned media were purified using MabSelect SuRe Protein A medium (GE Healthcare). SDS-PAGE images of the purified antibodies are provided in FIG. 4.

G. Binding Confirmation with Purified Antibodies

Figure 5:
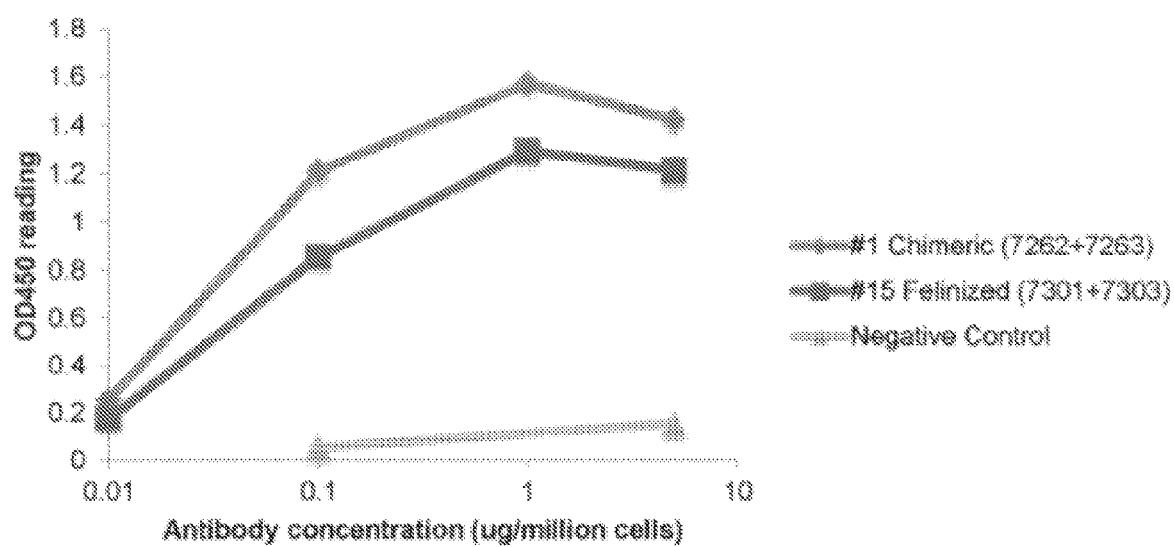
FIG. 5 is a graph showing the antigen binding dose response curves for particular chimeric and felinized antibodies.

Binding confirmation was done as previously described using the purified antibodies at multiple antibody concentrations. The antigen binding dose response curves are shown in FIG. 5. Nonlinear regression was used to analyze the data with GraphPad Prism, and an EC50 was calculated to determine the concentration of antibody that bound the antigen halfway between the baseline and maximum. The EC50 values for each independent curve and the average and standard deviation of the two curves are shown in FIG. 5. The fold increase in binding affinity over the parental antibody is provided in the table corresponding to FIG. 5 and shown below.

| Antibody # | OD450 at 0.1 ug | OD450 at 1 ug | Average fold change over chimeric |
|---|---|---|---|
| #1 (Chimeric) | 1.21 | 1.57 | 1.00x |
| #15 (Felinized) | 0.86 | 1.29 | 0.76x |

H. Sequences of the MHC306 Feline mAb Felinized Chains

The sequences of the MHC306 Feline mAb felinized chains are provided in FIGS. 6-13.

I. Summary

Felinization of MHC306 Feline mAb has been completed successfully. In total, nine fully felinized antibodies were designed, produced, and tested. One of these antibodies was selected for 0.1 liter scale-up and purification, and its antigen binding affinity was confirmed. The purified felinized antibody displayed potent and specific antigen binding affinity that is comparable to the parental antibody.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A felinized antibody or a fragment thereof that binds to feline CD11a and comprising the amino acid sequence of SEQ. ID NO: 5 and the amino acid sequence of SEQ. ID NO: 3.

2. The felinized antibody or the fragment of claim 1, wherein the felinized antibody contains the CDRs of the parental antibody TS1/22 produced from ATCC deposit number HB202.

3. The felinized antibody or the fragment of claim 1, provided in a veterinary composition formulation.

4. The felinized antibody or the fragment of claim 1, further comprising a feline Fc domains.

5. The felinized antibody or the fragment of claim 1, characterized by detectable antigen binding affinity using a MCH-4 cell binding assay.

6. The felinized antibody or the fragment of claim 5, wherein the felinized antibody or fragment has a relative antigen binding affinity of 0.30 compared to a chimeric parental antibody.

7. The felinized antibody or the fragment of claim 6, wherein the felinized antibody or fragment and the chimeric parental antibody include the same backbone Fc sequences.

8. The felinized antibody or the fragment of claim 1, characterized by a binding dose response of 0.86 at a concentration of 0.1 μg at OD450 or 1.29 at a concentration of 1 μg at OD450.

9. The felinized antibody or the fragment of claim 8, wherein the felinized antibody or fragment has a 0.76× fold change in binding affinity relative to a chimeric parental antibody.

10. The felinized antibody or the fragment of claim 9, wherein the felinized antibody or fragment and the chimeric parental antibody include the same backbone Fc sequences.

* * * * *

SEQUENCE LISTING

<160> NUMBER OF SEQ ID NOS: 16

<210> SEQ ID NO 1

```
<211> LENGTH: 117
<212> TYPE: PRT
<213> ORGANISM: Feline

<400> SEQUENCE: 1

Gln Val Gln Leu Val Gln Ser Gly Ala Glu Val Arg Lys Pro Gly Ala
1               5                   10                  15

Ser Val Lys Ile Phe Cys Lys Ala Ser Gly Tyr Thr Phe Thr Ser Tyr
                20                  25                  30

Tyr Ile His Trp Leu Arg Gln Thr Pro Glu Gln Gly Leu Glu Trp Met
            35                  40                  45

Gly Trp Ile Tyr Val Gly Asp Gly Asn Thr Arg Tyr Asn Gln Lys Phe
    50                  55                  60

Gln Gly Arg Leu Thr Leu Thr Ala Asp Lys Ser Thr Ser Thr Ala Tyr
65                  70                  75                  80

Met Glu Leu Ser Ser Leu Arg Ser Ala Asp Thr Ala Ile Tyr Phe Cys
                85                  90                  95

Ala Arg Gly Gly Asn Gly Tyr Phe Asp Tyr Trp Gly Gln Asp Thr Leu
            100                 105                 110

Val Thr Val Ser Ser
        115

<210> SEQ ID NO 2
<211> LENGTH: 351
<212> TYPE: DNA
<213> ORGANISM: Feline

<400> SEQUENCE: 2
caggtgcagc tggtgcagtc tggcgctgaa gtgcgaaagc ctggcgcctc cgtgaagatt    60
ttctgcaagg cctccggcta caccttcacc agctactaca tccactggct gcggcagacc   120
cctgagcagg gcctggaatg gatgggctgg atctatgtgg gcgacggcaa caccaggtac   180
aaccagaagt tccagggccg gctgaccctg accgccgaca gtctacctc  caccgcctac   240 atggaactgt cctccctgag atccgccgac accgccatct acttttgcgc cagaggcggc   300
aacggctact tcgactactg gggccaggac accctcgtga ccgtgtcctc t            351

<210> SEQ ID NO 3
<211> LENGTH: 117
<212> TYPE: PRT
<213> ORGANISM: Feline

<400> SEQUENCE: 3

Gln Val Gln Leu Val Gln Ser Gly Ala Glu Val Arg Lys Pro Gly Ala
1               5                   10                  15

Ser Val Lys Ile Phe Cys Lys Ala Ser Gly Tyr Thr Phe Thr Ser Tyr
                20                  25                  30

Tyr Ile His Trp Leu Arg Gln Thr Pro Glu Gln Gly Arg Glu Trp Ile
            35                  40                  45

Gly Trp Ile Tyr Val Gly Asp Gly Asn Thr Arg Tyr Asn Glu Lys Phe
    50                  55                  60

Gln Gly Arg Leu Thr Leu Thr Ala Asp Lys Ser Thr Ser Thr Ala Tyr
65                  70                  75                  80

Met Glu Leu Ser Ser Leu Arg Ser Ala Asp Thr Ala Ile Tyr Phe Cys
                85                  90                  95

Ala Arg Gly Gly Asn Gly Tyr Phe Asp Tyr Trp Gly Gln Asp Thr Leu
            100                 105                 110
```

Val Thr Val Ser Ser
    115

<210> SEQ ID NO 4
<211> LENGTH: 351
<212> TYPE: DNA
<213> ORGANISM: Feline

<400> SEQUENCE: 4
caggtgcagc tggtgcagtc tggcgctgaa gtgcgaaagc tggcgcctc cgtgaagatt       60 ttctgcaagg cctccggcta caccttcacc agctactaca tccactggct gcggcagacc      120
cccgagcagg gaagagaatg gatcggctgg atctacgtgg gcgacggcaa cacccggtac      180
aacgagaagt tccagggccg gctgaccctg accgccgaca gtctacctc caccgcctac      240 atggaactgt cctccctgag atccgccgac accgccatct acttttgcgc cagaggcggc      300
aacggctact cgactactg gggccaggac accctcgtga ccgtgtcctc t                351

<210> SEQ ID NO 5
<211> LENGTH: 117
<212> TYPE: PRT
<213> ORGANISM: Feline

<400> SEQUENCE: 5

Gln Val Gln Leu Val Gln Ser Gly Ala Glu Val Arg Thr Pro Gly Ala
1               5                   10                  15

Ser Val Lys Ile Phe Cys Lys Ala Ser Gly Tyr Thr Phe Thr Ser Tyr
            20                  25                  30

Tyr Ile His Trp Val Arg Gln Ser Pro Ala Gln Gly Arg Glu Trp Met
        35                  40                  45

Gly Trp Ile Tyr Val Gly Asp Gly Asn Thr Lys Tyr Asn Glu Arg Phe
    50                  55                  60

Gln Gly Arg Leu Thr Leu Thr Ala Asp Lys Ser Thr Ser Thr Ala Tyr
65                  70                  75                  80

Met Glu Leu Ser Ser Leu Arg Ser Ala Asp Thr Ala Met Tyr Phe Cys
                85                  90                  95

Ala Arg Gly Gly Asn Gly Tyr Phe Asp Tyr Trp Gly Gln Gly Ala Leu
            100                 105                 110

Val Thr Val Ser Ser
    115

<210> SEQ ID NO 6
<211> LENGTH: 351
<212> TYPE: DNA
<213> ORGANISM: Feline

<400> SEQUENCE: 6
caggtgcagc tggtgcagtc tggcgctgaa gtgcgaaccc ctggcgcctc cgtgaagatt       60
ttctgcaagg cctccggcta caccttcacc agctactaca tccactgggt gcgacagagc      120
cctgcccagg gcagagaatg gatgggctgg atctatgtgg gcgacggcaa caccaagtac      180
aacgagcggt tccagggccg gctgaccctg accgctgaca gtctacctc caccgcctac      240 atggaactgt cctccctgag atccgccgac accgccatgt acttttgcgc cagaggcggc      300
aacggctact cgactattg gggccagggc gctctcgtga ccgtgtcctc t                351

<210> SEQ ID NO 7
<211> LENGTH: 106
<212> TYPE: PRT

<213> ORGANISM: Feline

<400> SEQUENCE: 7

Asp Ile Val Met Thr Gln Thr Pro Leu Ser Leu Ser Val Thr Pro Gly
1               5                   10                  15

Glu Pro Ala Ser Ile Ser Cys Arg Ala Ser Gln Asp Val Ser Thr Ala
            20                  25                  30

Leu Asn Trp Tyr Leu Gln Lys Pro Gly Gln Ser Pro Arg Leu Leu Ile
        35                  40                  45

Tyr Trp Ala Ser Asn Arg His Ser Gly Val Pro Asp Arg Phe Ser Gly
    50                  55                  60

Ser Gly Ser Gly Thr Asp Tyr Thr Leu Arg Ile Ser Arg Val Glu Ala
65                  70                  75                  80

Asp Asp Val Gly Val Tyr Tyr Cys Gln Gln His Tyr Ser Ser Ser Leu
                85                  90                  95

Thr Phe Gly Pro Gly Thr Lys Leu Glu Ile
            100                 105

<210> SEQ ID NO 8
<211> LENGTH: 318
<212> TYPE: DNA
<213> ORGANISM: Feline

<400> SEQUENCE: 8
gacatcgtga tgacccagac ccctctgtcc ctgtctgtga cacctggcga gcctgcctcc      60
atctcctgca gagcctccca ggatgtgtct accgccctga actggtatct gcagaagcct     120
ggccagtctc ctcggctgct gatctactgg gcctccaaca cactctgg cgtgcccgac      180 agattctccg ctctggctc tggcaccgac tacaccctgc ggatctccag agtggaagcc     240
gacgacgtgg gcgtgtacta ctgccagcag cactactcct ccagcctgac ctttggccct     300
ggcaccaagc tggaaatc                                                   318

<210> SEQ ID NO 9
<211> LENGTH: 106
<212> TYPE: PRT
<213> ORGANISM: Feline

<400> SEQUENCE: 9

Asp Ile Val Met Thr Gln Thr Pro Leu Ser Leu Ser Val Thr Pro Gly
1               5                   10                  15

Glu Pro Ala Ser Ile Ser Cys Arg Ala Ser Gln Asp Val Ser Thr Ala
            20                  25                  30

Leu Ala Trp Tyr Leu Gln Lys Pro Gly Gln Ser Pro Arg Leu Leu Ile
        35                  40                  45

Tyr Trp Ala Ser Thr Arg His Ser Gly Val Pro Asp Arg Phe Ser Gly
    50                  55                  60

Ser Gly Ser Gly Thr Asp Tyr Thr Leu Arg Ile Ser Arg Val Glu Ala
65                  70                  75                  80

Asp Asp Val Gly Val Tyr Tyr Cys Gln Gln His Tyr Ser Ser Ser Leu
                85                  90                  95

Thr Phe Gly Pro Gly Thr Lys Leu Glu Ile
            100                 105

<210> SEQ ID NO 10
<211> LENGTH: 318
<212> TYPE: DNA
<213> ORGANISM: Feline

<400> SEQUENCE: 10

```
gacatcgtga tgacccagac ccctctgtcc ctgtctgtga cacctggcga gcctgcctcc    60
atctcctgca gagcctccca ggatgtgtct accgccctgg cctggtatct gcagaagcct   120
ggccagtctc ctcggctgct gatctactgg gcctccacca cactctggcg cgtgcccgac   180
agattctccg gctctggctc tggcaccgac tacaccctgc ggatctccag agtggaagcc   240
gacgacgtgg gcgtgtacta ctgccagcag cactactcct ccagcctgac ctttggccct   300
ggcaccaagc tggaaatc                                                 318
```

<210> SEQ ID NO 11
<211> LENGTH: 105
<212> TYPE: PRT
<213> ORGANISM: Feline

<400> SEQUENCE: 11

Asp Ile Val Met Thr Gln Pro Pro Ser Val Ser Gly Ala Leu Gly Gln
1               5                   10                  15

Thr Val Thr Ile Ser Cys Ala Gly Ser Gln Asp Val Ser Thr Ala Val
            20                  25                  30

Ala Trp Tyr Gln Gln Leu Thr Gly Lys Ala Pro Thr Leu Leu Ile Tyr
        35                  40                  45

Trp Ala Ser Thr Arg His Ser Ser Val Pro Asp Arg Phe Ser Gly Ser
    50                  55                  60

Gly Ser Gly Thr Thr Tyr Ser Leu Thr Ile Thr Gly Leu Gln Ala Glu
65                  70                  75                  80

Asp Glu Ala Asp Tyr Tyr Cys Gln Gln His Tyr Ser Ser Ser Leu Thr
                85                  90                  95

Phe Gly Ala Asp Thr Val Leu Gln Ala
            100                 105

<210> SEQ ID NO 12
<211> LENGTH: 315
<212> TYPE: DNA
<213> ORGANISM: Feline

<400> SEQUENCE: 12

```
gacatcgtga tgacccagcc cccttctgtg tctggcgctc tgggccagac cgtgaccatc    60
tcttgtgccg gctctcagga cgtgtccacc gccgtggctt ggtatcagca gctgaccggc   120
aaggccccca ccctgctgat ctactgggcc tccaccagac actcctccgt gcctgacaga   180
ttctccggct ctggctccgg caccacctac tccctgacaa tcaccggact gcaggccgag   240
gacgaggccg actactactg ccagcagcac tactcctcca gcctgacctt tggcgccgac   300
accgtgctgc aggct                                                   315
```

<210> SEQ ID NO 13
<211> LENGTH: 334
<212> TYPE: PRT
<213> ORGANISM: Feline

<400> SEQUENCE: 13

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser

```
            35                  40                  45
Gly Val His Thr Phe Pro Ala Val Leu Gln Ala Ser Gly Leu Tyr Ser
 50                  55                  60

Leu Ser Ser Met Val Thr Val Pro Ser Ser Arg Trp Leu Ser Asp Thr
 65                  70                  75                  80

Phe Thr Cys Asn Val Ala His Pro Pro Ser Asn Thr Lys Val Asp Lys
                 85                  90                  95

Thr Val Arg Lys Thr Asp His Pro Pro Gly Pro Lys Pro Cys Asp Cys
                100                 105                 110

Pro Lys Cys Pro Pro Pro Glu Met Leu Gly Gly Pro Ser Ile Phe Ile
            115                 120                 125

Phe Pro Pro Lys Pro Lys Asp Thr Leu Ser Ile Ser Arg Thr Pro Glu
            130                 135                 140

Val Thr Cys Leu Val Val Asp Leu Gly Pro Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
            195                 200                 205

Val Asn Ser Lys Ser Leu Pro Ser Pro Ile Glu Arg Thr Ile Ser Lys
210                 215                 220

Ala Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Lys
                245                 250                 255

Ser Phe His Pro Pro Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
            275                 280                 285

Asp Gly Thr Tyr Phe Val Tyr Ser Lys Leu Ser Val Asp Arg Ser His
            290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr Gln Ser Pro Gly
                325                 330

<210> SEQ ID NO 14
<211> LENGTH: 1008
<212> TYPE: DNA
<213> ORGANISM: Feline

<400> SEQUENCE: 14
gctagcacca ccgcccttc cgtgttccct ctggccccctt cttgtggcac cacctctggc      60
gctacagtgg ccctggcttg tctggtgctg ggctacttcc ctgagcccgt gaccgtgtcc     120
tggaactctg gcgcactgac atccggcgtg cacaccttcc ctgctgtgct gcaggcttcc     180
ggcctgtact ccctgtcctc tatggtcacc gtgcccctcca gccggtggct gtccgatacc     240
ttcacctgta acgtggccca ccctcccagc aacaccaagg tggacaagac cgtgcgcaag     300
accgaccacc ctcctggccc taagccttgc gactgcccta gtgcccaccc cctgaaatg      360 ctgggcggac ctagcatctt catcttccca cccaagccca aggacaccct gtccatctcc     420
cggacccctg aagtgacctg cctggtggtg gatctgggcc ctgacgactc cgacgtgcag     480
```

-continued

```
atcacttggt tgtggacaa cacccaggtg tacacagcca agacctcccc cagagaggaa    540
cagttcaact ccacctaccg ggtggtgtcc gtgctgccca tcctgcacca ggattggctg    600
aagggcaaag aattcaagtg caaagtgaac tccaagtccc tgcccagccc catcgagcgg    660
accatctcta aggccaaggg ccagcctcac gagcctcagg tgtacgtgct gcctcccgcc    720
caggaagaac tgtcccggaa caaagtgtcc gtgacctgtc tgatcaagtc cttccaccca    780
cccgatatcg ccgtggaatg ggagatcacc ggccagcccg agcccgagaa caactacaga    840
accacccctc cccagctgga ctctgacggc acctacttcg tgtactccaa gctgtccgtg    900
gacagatccc actggcagcg gggcaacacc tacacctgtt ccgtgtctca cgaggccctg    960
cactcccacc acacccagaa gtctctgacc cagtcccccg gctagtaa              1008
```

<210> SEQ ID NO 15
<211> LENGTH: 111
<212> TYPE: PRT
<213> ORGANISM: Feline

<400> SEQUENCE: 15

Lys Arg Ser Asp Ala Gln Pro Ser Val Phe Leu Phe Gln Pro Ser Leu
1               5                   10                  15

Asp Glu Leu His Thr Gly Ser Ala Ser Ile Val Cys Ile Leu Asn Asp
                20                  25                  30

Phe Tyr Pro Lys Glu Val Asn Val Lys Trp Lys Val Asp Gly Val Val
            35                  40                  45

Gln Thr Lys Ala Ser Lys Glu Ser Thr Thr Glu Gln Asn Ser Lys Asp
        50                  55                  60

Ser Thr Tyr Ser Leu Ser Ser Thr Leu Thr Met Ser Arg Thr Glu Tyr
65                  70                  75                  80

Gln Ser His Glu Lys Phe Ser Cys Glu Val Thr His Lys Ser Leu Ala
                85                  90                  95

Ser Thr Leu Val Lys Ser Phe Asn Arg Ser Glu Cys Gln Arg Glu
                100                 105                 110

<210> SEQ ID NO 16
<211> LENGTH: 336
<212> TYPE: DNA
<213> ORGANISM: Feline

<400> SEQUENCE: 16

```
aagagatccg acgcccagcc ctccgtgttc ctgttccagc cttctctgga cgagctgcac    60
accggctccg cctccatcgt gtgcatcctg aacgacttct accccaaaga agtgaacgtg   120
aagtggaagg tggacggcgt ggtgcagacc aaggcctcca agagtccac caccgagcag   180 aactccaagg actccaccta ctccctgtcc tccaccctga ccatgtcccg gaccgagtac   240
cagtcccacg agaagttcag ctgcgaagtg acccacaagt ccctggccag caccctcgtg   300
aagtccttca acagatccga gtgccagaga gagtaa                             336
```